United States Patent
Ye et al.

(10) Patent No.: US 11,684,601 B2
(45) Date of Patent: Jun. 27, 2023

(54) TREATMENT OF CANCER WITH COMBINATIONS OF AGENTS

(71) Applicant: The Board of Trustees of the Leland Stanford Junior University, Stanford, CA (US)

(72) Inventors: Jiangbin Ye, Stanford, CA (US); Yang Li, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 146 days.

(21) Appl. No.: 16/792,012

(22) Filed: Feb. 14, 2020

(65) Prior Publication Data

US 2020/0261393 A1    Aug. 20, 2020

Related U.S. Application Data

(60) Provisional application No. 62/807,436, filed on Feb. 19, 2019.

(51) Int. Cl.
| | | |
|---|---|---|
| A61K 31/22 | (2006.01) | |
| A61P 35/00 | (2006.01) | |
| A61K 9/00 | (2006.01) | |
| A61K 31/203 | (2006.01) | |

(52) U.S. Cl.
CPC ............ A61K 31/22 (2013.01); A61K 9/0053 (2013.01); A61K 31/203 (2013.01); A61P 35/00 (2018.01)

(58) Field of Classification Search
CPC .... A61K 31/203; A61K 31/22; A61K 9/0053; A61P 35/00
USPC ........................................................ 514/547
See application file for complete search history.

(56) References Cited

U.S. PATENT DOCUMENTS

| | | | | |
|---|---|---|---|---|
| 10,765,654 | B2 * | 9/2020 | Jaworski | A61P 35/00 |
| 11,147,784 | B2 * | 10/2021 | Rabinowitz | A61K 31/519 |
| 2007/0111979 | A1 * | 5/2007 | Robert Bishop | A61P 35/00 514/183 |
| 2014/0142152 | A1 * | 5/2014 | Jaworski | A61P 35/00 514/393 |
| 2016/0374971 | A1 * | 12/2016 | Rabinowitz | A61K 45/06 514/43 |

OTHER PUBLICATIONS

Zage PE (A novel therapeutic combination for neuroblastoma: the vascular endothelial growth factor receptor/epidermal growth factor receptor/rearranged during transfection inhibitor vandetanib with 13-cis-retinoic acid. Cancer. May 15, 2010;116(10).*
Sonawane P, Cho HE, Tagde A, Verlekar D, Yu AL, Reynolds CP, Kang MH. Metabolic characteristics of 13-cis-retinoic acid (isotretinoin) and anti-tumour activity of the 13-cis-retinoic acid metabolite 4-oxo-13-cis-retinoic acid in neuroblastoma. Br J Pharmacol. Dec. 2014;171(23):5330-44. doi: 10.1111/bph.12846. PMID:.*
Li et al. (2020) "Cell Death and Disease Acetate supplementation restores chromatin accessibility and promotes tumor cell differentiation under hypoxia") 11:102.
Li et al. (2019) Abstract 3798: Acetate supplementation eliminates hypoxia mediated resistance to differentiation therapy in neuroblastoma cells "Experimental and Molecular Therapeutics" Abstract 3798:.

* cited by examiner

*Primary Examiner* — Svetlana M Ivanova
(74) *Attorney, Agent, or Firm* — Pamela J. Sherwood; Bozicevic, Field & Francis LLP

(57) ABSTRACT

Methods are provided for the treatment of cancer by administering a combination of metabolic interventions to differentiate the cancer cells. The effect on the targeted cancer cell is enhanced relative to a regimen in which a single agent is used; and the effect may be synergistic relative to a regimen in which a single agent is used.

12 Claims, 13 Drawing Sheets

TREATMENT OF CANCER WITH COMBINATIONS OF AGENTS

CROSS-REFERENCE TO RELATED APPLICATIONS

This application claims the benefit of U.S. Provisional Patent Application No. 62/807,436, filed Feb. 19, 2019, which application is incorporated herein by reference in its entirety.

FEDERALLY SPONSORED RESEARCH AND DEVELOPMENT

This invention was made with Government support under contract CA184239 awarded by the National Institutes of Health. The Government has certain rights in the invention.

BACKGROUND

Cell differentiation is the process that a stem/progenitor cell becomes specialized cells. Proper cell differentiation processes require a signaling cascade to activate the transcriptional machinery, and accessibility to chromosomes. Together tissue—specific differentiation marker are expressed, and cells can differentiate.

Metabolic reprogramming during cell differentiation has been reported by previous studies. Generally, undifferentiated cells, including normal embryonic stem cell and undifferentiated cancer cells, primarily utilize aerobic glycolysis, but switch to oxidative phosphorylation when they are induced to differentiate. The distinct metabolic phenotype between differentiated cell and undifferentiated cell indicates a critical role of mitochondrial metabolism in differentiation.

Neuroblastoma is the most common and deadliest solid tumor in childhood. It is derived from the neural crest cells that fail to exit the cell cycle and differentiate. Most neuroblastomas occur spontaneously, but a small percentage appear to be inherited. Some markers such as MYCN oncogene amplification, hyperdiploidy, histopathology correlate with progression and prognosis. About 40 to 50% of children have localized or regional disease at diagnosis; 50 to 60% have metastases at diagnosis. Neuroblastoma may metastasize to bone marrow, bone, liver, lymph nodes, or, less commonly, skin or brain.

Methods of treating cancers, including neuroblastoma, are of great clinical interest.

SUMMARY

Methods are provided for the treatment of cancer, including without limitation neuroblastoma, and including high risk neuroblastoma, squamous cell carcinoma, CML, and the like cancer types that can respond to RA treatment, by administering a combination of agents that provide for metabolic interventions, which induce differentiation of the cancer cells. In some embodiments, the combination of agents provides a synergistic effect relative to the administration of an agent as a monotherapy. In various embodiments, the combination of agents may be administered in a therapeutic regimen that includes conventional treatment, e.g. targeted anti-tumor antibodies, chemotherapy, radiation therapy, surgery, and the like.

In an embodiment, administration of an effective dose of retinoic acid is combined with administration of an agent that provides acetate supplementation, e.g. a glyceryltriacetate (GTA) compound. Acetate supplementation does not significantly alter cancer cell differentiation as a single agent, but it can restore the sensitivity of cells to RA-induced differentiation. Without being bound by the theory, it is believed that increasing histone acetylation under hypoxia can re-sensitize hypoxic tumor cells to differentiation therapy. Acetate supplementation with RA therapy is an efficacious therapeutic approach to increase the sensitivity of cancer to differentiation therapy.

The therapeutic forms of RA include all trans retinoic acid (ATRA, tretinoin); 9-cis-retinoic acid (Alitretinoin); and 13-cis-retinoic acid (Isotretinoin), and other synthetic RA analogs. In some embodiments the retinoic acid is 13-cis-retinoic acid.

According to another embodiment, articles oSPELLf manufacture are provided. The articles of manufacture, also referred to as kits, include packaging material and a therapeutic combination of glyceryltriacetate (GTA) compound and a retinoic acid, wherein the article of manufacture also includes a label or package insert. According to another aspect of the invention, use of a glyceryltriacetate (GTA) compound in the manufacture of a medicament for the treatment of cancer is provided.

A benefit of the present invention can be the use of lowered doses of the agents relative to the dose required as a single agent. A benefit of the present invention can also, or alternatively, be a decrease in the length of time required for treatment, relative to the length of time required for treatment as a single agent. A benefit of the present invention can also, or alternatively, be an enhanced response relative to the response observed after treatment with a single agent.

Methods of administration include, without limitation, oral administration, systemic administration, intra-tumoral administration, etc. Usually the active agent (i) is administered within about a period of about 45 days, about 30 days, about 21 days, about 14 days, about 10 days, about 8 days, about 7 days, about 6 days, about 5 days, about 4 days, about 3 days, about 2 days, about 1 day or substantially the same day as an agent (ii) and/or (iii). In some embodiments an agent (i) is administered prior to an agent (ii) and/or (iii). In some embodiments an agent (i) is administered after an agent (ii) and/or (iii). The agents can be considered to be combined if administration scheduling is such that the serum level of both agents is at a therapeutic level at the same time. Administration may be repeated as necessary for differentiation of the cancer cell population.

DETAILED DESCRIPTION OF THE EMBODIMENTS

Figure 1:
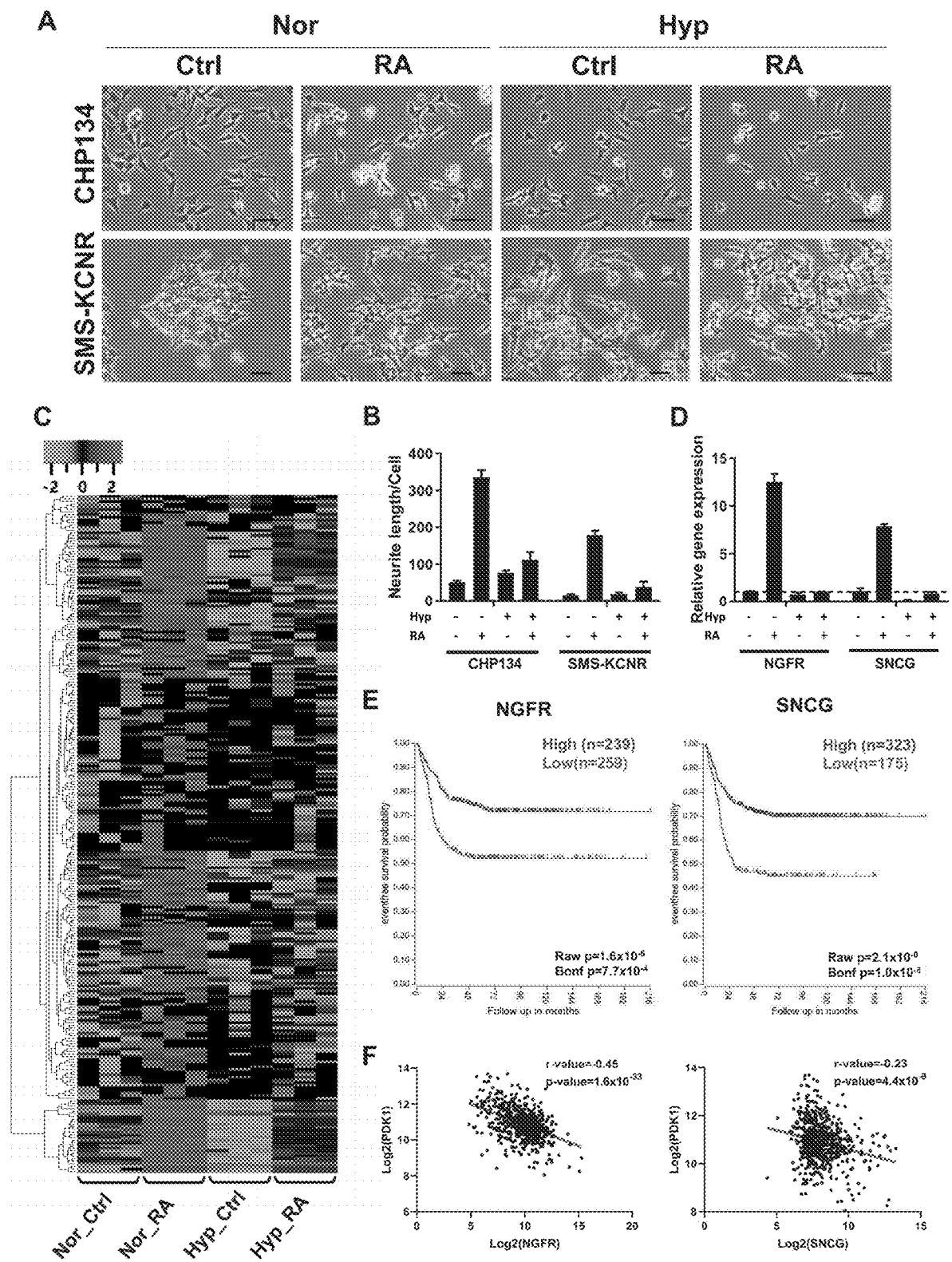
FIG. 1. Hypoxia disrupts RA-induced differentiation by suppressing the expression of differentiation markers in neuroblastoma cells. (A) CHP134 and SMS-KCNR cells were treated with 10 μM RA for 48 h under normoxia or hypoxia. Representative image from each treatment group showed the morphologic changes. Scale bar: 50 μm. (B) Quantification of neurite outgrowth in (A) with NeuronJ, a plugin in the ImageJ package. (C) Heatmap and hierarchical clustering of the potential differentiation markers that were induced by RA treatment but repressed by hypoxia treatment. Gene expression levels were determined by RNA-Seq (n=3). (D) NGFR and SNCG expression levels in CHP134 cells treated with 10 μM RA or DMSO under normoxia or hypoxia (n=3). (E) Overall survival of neuroblastoma patients grouped by NGFR or SNCG expression level. (F) The negative correlation between the expression of differentiation markers and hypoxic marker PDK1 in neuroblastoma samples. (The analyses in E-F were performed on publicly available dataset from R2: Genomic Analysis and Visualization Platform).

Methods are provided for the treatment of cancer by administering a combination of agents that provide for metabolic interventions, which induce differentiation of the cancer cells. In some embodiments, the combination of agents provides a synergistic effect relative to the administration of an agent as a monotherapy. In various embodiments, the combination of agents may be administered in a therapeutic regimen that includes conventional treatment, e.g. targeted anti-tumor antibodies, chemotherapy, radiation therapy, surgery, and the like.

To facilitate an understanding of the invention, a number of terms are defined below.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. 1, Cold Spring Harbor Laboratory (1998); and Harlow and Lane, Antibodies: A Laboratory Manual, Cold Spring Harbor Laboratory; (1988).

A "patient" for the purposes of the present invention includes both humans and other animals, particularly mammals, including pet and laboratory animals, e.g. mice, rats, rabbits, etc. Thus the methods are applicable to both human therapy and veterinary applications. In one embodiment the patient is a mammal, preferably a primate. In other embodiments the patient is human.

The terms "subject," "individual," and "patient" are used interchangeably herein to refer to a mammal being assessed for treatment and/or being treated. In an embodiment, the mammal is a human. The terms "subject," "individual," and "patient" encompass, without limitation, individuals having cancer. Subjects may be human, but also include other mammals, particularly those mammals useful as laboratory models for human disease, e.g. mouse, rat, etc.

The terms "cancer," "neoplasm," and "tumor" are used interchangeably herein to refer to cells which exhibit autonomous, unregulated growth, such that they exhibit an aberrant growth phenotype characterized by a significant loss of control over cell proliferation. Cells of interest for detection, analysis, or treatment in the present application include precancerous (e.g., benign), malignant, pre-metastatic, metastatic, and non-metastatic cells. Cancers of virtually every tissue are known. The phrase "cancer burden" refers to the quantum of cancer cells or cancer volume in a subject. Reducing cancer burden accordingly refers to reducing the number of cancer cells or the cancer volume in a subject. The term "cancer cell" as used herein refers to any cell that is a cancer cell or is derived from a cancer cell e.g. clone of a cancer cell. Many types of cancers are known to those of skill in the art, including solid tumors such as carcinomas, sarcomas, glioblastomas, melanomas, lymphomas, myelomas, etc., and circulating cancers such as leukemias. Examples of cancer include but are not limited to, ovarian cancer, breast cancer, colon cancer, lung cancer, prostate cancer, hepatocellular cancer, gastric cancer, pancreatic cancer, cervical cancer, ovarian cancer, liver cancer, bladder cancer, cancer of the urinary tract, thyroid cancer, renal cancer, carcinoma, melanoma, head and neck cancer, and brain cancer. In some embodiments the cancer is other than a glioma.

Cancers that have been treated with retinoic acid and that can benefit from acetate supplementation include, without limitation, juvenile chronic myelogenous leukemia (CML), neuroblastoma, including high risk neuroblastoma, recurrent cervical cancer, squamous cell head and neck cancer, and squamous cell skin carcinoma. In some embodiments the cancer is neuroblastoma. In some embodiments the neuroblastoma is high risk neuroblastoma.

The "pathology" of cancer includes all phenomena that compromise the well-being of the patient. This includes, without limitation, abnormal or uncontrollable cell growth, metastasis, interference with the normal functioning of neighboring cells, release of cytokines or other secretory products at abnormal levels, suppression or aggravation of inflammatory or immunological response, neoplasia, premalignancy, malignancy, invasion of surrounding or distant tissues or organs, such as lymph nodes, etc.

As used herein, the terms "cancer recurrence" and "tumor recurrence," and grammatical variants thereof, refer to further growth of neoplastic or cancerous cells after diagnosis of cancer. Particularly, recurrence may occur when further cancerous cell growth occurs in the cancerous tissue. "Tumor spread," similarly, occurs when the cells of a tumor disseminate into local or distant tissues and organs; therefore tumor spread encompasses tumor metastasis. "Tumor invasion" occurs when the tumor growth spread out locally to compromise the function of involved tissues by compression, destruction, or prevention of normal organ function.

As used herein, the term "metastasis" refers to the growth of a cancerous tumor in an organ or body part, which is not directly connected to the organ of the original cancerous tumor. Metastasis will be understood to include micrometastasis, which is the presence of an undetectable number of cancerous cells in an organ or body part which is not directly connected to the organ of the original cancerous tumor. Metastasis can also be defined as several steps of a process, such as the departure of cancer cells from an original tumor site, and migration and/or invasion of cancer cells to other parts of the body.

The term "sample" with respect to a patient encompasses blood and other liquid samples of biological origin, solid tissue samples such as a biopsy specimen or tissue cultures or cells derived therefrom and the progeny thereof. The definition also includes samples that have been manipulated in any way after their procurement, such as by treatment with reagents; washed; or enrichment for certain cell populations, such as cancer cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's cancer cell, e.g., a sample comprising polynucleotides and/or polypeptides that is obtained from a patient's cancer cell (e.g., a cell lysate or other cell extract comprising polynucleotides and/or polypeptides); and a sample comprising cancer cells from a patient. A biological sample comprising a cancer cell from a patient can also include non-cancerous cells.

The term "diagnosis" is used herein to refer to the identification of a molecular or pathological state, disease or condition, such as the identification of a molecular subtype of breast cancer, prostate cancer, or other type of cancer.

The term "prognosis" is used herein to refer to the prediction of the likelihood of cancer-attributable death or progression, including recurrence, metastatic spread, and drug resistance, of a neoplastic disease, such as ovarian cancer. The term "prediction" is used herein to refer to the act of foretelling or estimating, based on observation, experience, or scientific reasoning. In one example, a physician may predict the likelihood that a patient will survive, following surgical removal of a primary tumor and/or chemotherapy for a certain period of time without cancer recurrence.

As used herein, the terms "treatment," "treating," and the like, refer to administering an agent, or carrying out a procedure, for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, may include treatment of a tumor in a mammal, particularly in a human, and includes: (a) preventing the disease or a symptom of a disease from occurring in a subject which may be predisposed to the disease but has not yet been diagnosed as having it (e.g., including diseases that may be associated with or caused by a primary disease; (b) inhibiting the disease, i.e., arresting its development; and (c) relieving the disease, i.e., causing regression of the disease.

Treating may refer to any indicia of success in the treatment or amelioration or prevention of a cancer, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with cancer or other diseases. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of the agents described herein. When administered in combination, each component can be administered at the same time or sequentially in any order at different points in time. Thus, each component can be administered separately but sufficiently closely in time so as to provide the desired therapeutic effect.

"Concomitant administration" of active agents in the methods of the invention means administration with the reagents at such time that the agents will have a therapeutic effect at the same time. Such concomitant administration may involve concurrent (i.e. at the same time), prior, or subsequent administration of the agents. A person of ordinary skill in the art would have no difficulty determining the appropriate timing, sequence and dosages of administration for particular drugs and compositions of the present invention.

As used herein, endpoints for treatment will be given a meaning as known in the art and as used by the Food and Drug Administration.

Overall survival is defined as the time from randomization until death from any cause, and is measured in the intent-to-treat population. Survival is considered the most reliable cancer endpoint, and when studies can be conducted to adequately assess survival, it is usually the preferred endpoint. This endpoint is precise and easy to measure, documented by the date of death. Bias is not a factor in endpoint measurement. Survival improvement should be analyzed as a risk-benefit analysis to assess clinical benefit. Overall survival can be evaluated in randomized controlled studies. Demonstration of a statistically significant improvement in overall survival can be considered to be clinically significant if the toxicity profile is acceptable, and has often supported new drug approval. A benefit of the methods of the invention can include increased overall survival of patients.

Endpoints that are based on tumor assessments include DFS, ORR, TTP, PFS, and time-to-treatment failure (TTF). The collection and analysis of data on these time-dependent endpoints are based on indirect assessments, calculations, and estimates (e.g., tumor measurements). Disease-Free Survival (DFS) is defined as the time from randomization until recurrence of tumor or death from any cause. The most frequent use of this endpoint is in the adjuvant setting after definitive surgery or radiotherapy. DFS also can be an important endpoint when a large percentage of patients achieve complete responses with chemotherapy.

Objective Response Rate. ORR is defined as the proportion of patients with tumor size reduction of a predefined amount and for a minimum time period. Response duration usually is measured from the time of initial response until documented tumor progression. Generally, the FDA has defined ORR as the sum of partial responses plus complete responses. When defined in this manner, ORR is a direct measure of drug antitumor activity, which can be evaluated in a single-arm study.

Time to Progression and Progression-Free Survival. TTP and PFS have served as primary endpoints for drug approval. TTP is defined as the time from randomization until objective tumor progression; TTP does not include deaths. PFS is defined as the time from randomization until objective tumor progression or death. The precise definition of tumor progression is important and should be carefully detailed in the protocol.

Retinoic acid (RA). Retinoic acid is a metabolite of vitamin A (retinol) that mediates the functions of vitamin A required for growth and development. The therapeutic forms of RA include all trans retinoic acid (ATRA, tretinoin); 9-cis-retinoic acid (Alitretinoin); and 13-cis-retinoic acid (Isotretinoin). 13-cis-retinoic acid is most commonly used for the treatment of neuroblastoma.

Retinoic acid acts by binding to the retinoic acid receptor (RAR), which is bound to DNA as a heterodimer with the retinoid X receptor (RXR) in regions called retinoic acid response elements (RAREs). Retinoic acid receptors mediate transcription of different sets of genes controlling differentiation of a variety of cell types, thus the target genes regulated can provide for differentiation of cancer cells to a non-pathogenic phenotype. As demonstrated herein, the effectiveness on the desired target genes is improved with acetate supplementation.

Administration of RA is usually oral. Where the RA is isotretinoin, the dosage may range from at least 10, at least 25, least 50, at least 100, at least 200 and up to about 1000, up to about 750, up to about 500 mg/m$^2$/day.

Dosage of isotretinoin for the treatment of CML may be, for example, 100 mg/m$^2$/day orally, and up to 200 mg/m$^2$/day. Complete response for CML may be defined as white blood cell (WBC) normalization and resolution of organomegaly and partial response may be defined as a greater than 50% decrease in WBC count and organomegaly. An example of dosage of isotretinoin for the treatment of neuroblastoma may be, for example, 160 mg/m$^2$/day PO divided in 2 divided doses for 14 days repeated every 28 days for 6 cycles. An example of isotretinoin for the treatment of recurrent cervical cancer may be, for example, 1 mg/kg/day PO (rounded to the nearest 10 mg) divided into 2 doses. An example of dosage of isotretinoin for the treatment of squamous cell carcinoma is 50 mg/m$^2$/day PO, or 1 mg/kg/day PO. Isotretinoin is often administered in combination with interferon alfa, which may be administered in combination with an acetate supplementation agent.

Acetate supplementation Agent. An acetate supplementation agent increases levels of acetate in a cell. In some embodiments the agent is a glyceryltriacetate (GTA). GTA is a triglyceride 1,2,3-triacetoxypropane and is also known at least as triacetin; glyceryltriacetate, glycerin triacetate; 1,2,3-propanetriyl triacetate; Enzactin; Fungacetin, Glycerin triacetate; Triacetylglycerol; glycerol triacetate; Glyped; kesscoflex TRA; Tracetine; Vanay, Glycerol triacetate tributyrin; triacetyl glycerine; and Propane-1,2,3-triyltriacetate.

GTA can be orally administered. The dosage may be, for example, at least 25, at least 50, at least 75, at least 100, at least 250, at least 500, at least 750, at least 1000, at least 2000, at least 3000, at least 4000 mg/kg/daily, and may be up to 5000 mg/kg, up to 4000, up to 3000, up to 2000, up to 1000 mg/kg/daily.

In some embodiments, the total amount of GTA compound administered to the subject in a single day is between 0.1 and 100 g/kg body weight. In certain embodiments, the GTA compound is administered to the subject more than once and wherein the frequency of administration is at least once per month, once per week, every other day, or once per day. In some embodiments, the GTA compound is administered to the subject in a pharmaceutical composition. In some embodiments, the subject does not have Canavan disease. In some embodiments, the subject is a human. In certain embodiments, the subject is not undergoing treatment with the GTA compound for a non-cancer indication. In some embodiments, the subject is free of any indications otherwise calling for treatment with the GTA compound.

In embodiments of the invention, an amount of GTA compound in a dose administered to a subject as a treatment for a cancer is significantly higher than an amount of GTA suitable for use as a pharmaceutical excipient or carrier, for example, for inclusion in a pharmaceutical product as an excipient or carrier for an active pharmaceutical ingredient. The absolute amount will depend upon a variety of factors including the concurrent treatment, the number of doses and the individual patient parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Multiple doses of compounds of the invention are also contemplated. In some instances, a compound of the invention, (e.g. GTA) can be administered at least daily, every other day, weekly, every other week, monthly, etc. Doses may be administered once per day or more than once per day, for example, 2, 3, 4, 5, or more times in one 24 hour period.

Simultaneous administration typically means that both compounds enter the patient at precisely the same time. However, simultaneous administration also includes the possibility that the acetate supplementation agent and retinoic acid enter the patient at different times, but the difference in time is sufficiently miniscule that the first administered compound is not provided the time to take effect on the patient before entry of the second administered compound. Such delayed times typically correspond to less than 1 minute, and more typically, less than 30 seconds. In one example, wherein the compounds are in solution, simultaneous administration can be achieved by administering a solution containing the combination of compounds. In another example, simultaneous administration of separate solutions, one of which contains the acetate supplementation agent and the other of which contains retinoic acid, can be employed. In one example wherein the compounds are in solid form, simultaneous administration can be achieved by administering a composition containing the combination of compounds. Alternatively, simultaneous administration can be achieved by administering two separate compositions, one comprising the acetate supplementation agent and the other comprising retinoic acid.

In other embodiments, the acetate supplementation agent and retinoic acid are not administered simultaneously. In some embodiments, the acetate supplementation agent is administered before retinoic acid. In other embodiments, retinoic acid is administered before the acetate supplementation agent. In other embodiments, the first administered compound is provided time to take effect on the patient before the second administered compound is administered. Generally, the difference in time does not extend beyond the time for the first administered compound to complete its effect in the patient, or beyond the time the first administered compound is completely or substantially eliminated or deactivated in the patient.

In some embodiments, the retinoic acid is administered in a therapeutically effective amount or dosage. A "therapeutically effective amount" is an amount of retinoic acid that, when administered to a patient by itself, effectively treats neuroblastoma. An amount that proves to be a "therapeutically effective amount" in a given instance, for a particular subject, may not be effective for 100% of subjects similarly treated for the disease or condition under consideration, even though such dosage is deemed a "therapeutically effective amount" by skilled practitioners. The amount of the compound that corresponds to a therapeutically effective amount is strongly dependent on the type of cancer, stage of the cancer, the age of the patient being treated, and other facts. In general, therapeutically effective amounts, e.g., retinoic acid, are known in the art.

In other embodiments, the retinoic acid is administered in a sub-therapeutically effective amount or dosage. A sub-therapeutically effective amount is an amount of that, when administered to a patient by itself, does not completely inhibit over time the biological activity of the intended target.

Whether administered in therapeutic or sub-therapeutic amounts, the combination of the acetate supplementation agent and retinoic acid should be effective in treating cancer, e.g. neuroblastoma. For example, a subtherapeutic amount of retinoic acid can be an effective amount if, when combined with an acetate supplementation agent, the combination is effective in the treatment of neuroblastoma.

In some embodiments, the combination of compounds exhibits a synergistic effect (i.e., greater than additive effect) in the treatment of neuroblastoma. The term "synergistic effect" refers to the action of two agents, such as, for example, an acetate supplementation agent and retinoic acid, producing an effect, for example, slowing the symptomatic progression of cancer, e.g. neuroblastoma, or symptoms thereof, which is greater than the simple addition of the effects of each drug administered alone.

Different dosage regimens can be used to treat cancer, e.g. neuroblastoma. In some embodiments, a daily dosage, such as any of the exemplary dosages described above, is administered once, twice, three times, or four times a day for three, four, five, six, seven, eight, nine, or ten days. Depending on the stage and severity of the cancer, a shorter treatment time (e.g., up to five days) can be employed along with a high dosage, or a longer treatment time (e.g., ten or more days, or weeks, or a month, or longer) can be employed along with a low dosage. In some embodiments, a once- or twice-daily dosage is administered every other day. In some embodiments, each dosage contains both an acetate supplementation agent and retinoic acid to be delivered as a single dosage, while in other embodiments each dosage contains an acetate supplementation agent or retinoic acid to be delivered as separate dosages.

The agents can be administered via any of the accepted modes of administration or agents known in the art. The compounds can be administered, for example, orally, nasally, parenterally (intravenous, intramuscular, or subcutaneous), topically, transdermally, intravaginally, intravesically, intracisternally, or rectally. The dosage form can be, for example, a solid, semi-solid, lyophilized powder, or liquid dosage forms, such as for example, tablets, pills, soft elastic or hard gelatin capsules, powders, solutions, suspensions, suppositories, aerosols, or the like, preferably in unit dosage forms suitable for simple administration of precise dosages. A particular route of administration is oral, particularly one in which a convenient daily dosage regimen can be adjusted according to the degree of severity of the disease to be treated.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

Methods of Use

Methods are provided for treating or reducing primary or metastatic cancer, including without limitation juvenile chronic myelogenous leukemia (CML), neuroblastoma, including high risk neuroblastoma, recurrent cervical cancer, squamous cell head and neck cancer, and squamous cell skin carcinoma. In some embodiments the cancer is neuroblastoma. In some embodiments the neuroblastoma is high risk neuroblastoma. The cancer is treated in a regimen comprising contacting the targeted cells with a combination of (i) retinoic acid, e.g. isotretinoin; and (ii) an agent that supplements acetate in the cancer cells, e.g. glyceryltriacetate (GTA). Such methods include administering to a subject in need of treatment a therapeutically effective amount or an effective dose of the combined agents of the invention. It should be understood that there is little to no differentiative activity of GTA as a single agent, but in a combined therapy it enhances the activity of retinoic acid.

Effective doses of the combined agents of the present invention for the treatment of cancer vary depending upon many different factors, including means of administration, target site, physiological state of the patient, whether the patient is human or an animal, other medications administered, and whether treatment is prophylactic or therapeutic. Usually, the patient is a human, but nonhuman mammals may also be treated, e.g. companion animals such as dogs, cats, horses, etc., laboratory mammals such as rabbits, mice, rats, etc., and the like. Treatment dosages can be titrated to optimize safety and efficacy.

In some embodiments, the therapeutic dosage of each agent may range from about 0.0001 to 5000 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration daily, every other day, every third day, weekly, etc. Intervals can also be irregular as indicated by measuring blood levels of the therapeutic entity in the patient. Alternatively, therapeutic entities of the present invention can be administered as a sustained release formulation, in which case less frequent administration is required.

Chemotherapeutic agents that can be administered in combination with an anti-CD93 ABD polypeptide or engineered cell include, without limitation, abitrexate, adriamycin, adrucil, amsacrine, asparaginase, anthracyclines, azacitidine, azathioprine, bicnu, blenoxane, busulfan, bleomycin, camptosar, camptothecins, carboplatin, carmustine, cerubidine, chlorambucil, cisplatin, cladribine, cosmegen, cytarabine, cytosar, cyclophosphamide, cytoxan, dactinomycin, docetaxel, doxorubicin, daunorubicin, ellence, elspar, epirubicin, etoposide, fludarabine, fluorouracil, fludara, gemcitabine, gemzar, hycamtin, hydroxyurea, hydrea, idamycin, idarubicin, ifosfamide, ifex, irinotecan, lanvis, leukeran, leustatin, matulane, mechlorethamine, mercaptopurine, methotrexate, mitomycin, mitoxantrone, mithramycin, mutamycin, myleran, mylosar, navelbine, nipent, novantrone, oncovin, oxaliplatin, paclitaxel, paraplatin, pentostatin, platinol, plicamycin, procarbazine, purinethol, ralitrexed, taxotere, taxol, teniposide, thioguanine, tomudex, topotecan, valrubicin, velban, vepesid, vinblastine, vindesine, vincristine, vinorelbine, VP-16, and vumon.

Targeted therapeutics that can be administered in combination with retinoic acid and GTA may include, without limitation, tyrosine-kinase inhibitors, such as Imatinib mesylate (Gleevec, also known as STI-571), Gefitinib (Iressa, also known as ZD1839), Erlotinib (marketed as Tarceva), Sorafenib (Nexavar), Sunitinib (Sutent), Dasatinib (Sprycel), Lapatinib (Tykerb), Nilotinib (Tasigna), and Bortezomib (Velcade); Janus kinase inhibitors, such as tofacitinib; ALK inhibitors, such as crizotinib; Bcl-2 inhibitors, such as obatoclax, venclexta, and gossypol; FLT3 inhibitors, such as midostaurin (Rydapt), IDH inhibitors, such as AG-221, PARP inhibitors, such as Iniparib and Olaparib; PI3K inhibitors, such as perifosine; VEGF Receptor 2 inhibitors, such as Apatinib; AN-152 (AEZS-108) doxorubicin linked to [D-Lys(6)]-LHRH; Braf inhibitors, such as vemurafenib, dabrafenib, and LGX818; MEK inhibitors, such as trametinib; CDK inhibitors, such as PD-0332991 and LEE011; Hsp90 inhibitors, such as salinomycin; and/or small molecule drug conjugates, such as Vintafolide; serine/threonine kinase inhibitors, such as Temsirolimus (Torisel), Everolimus (Afinitor), Vemurafenib (Zelboraf), Trametinib (Mekinist), and Dabrafenib (Tafinlar).

A combination of retinoic acid and GTA may be administered in combination with an immunomodulator, such as a cytokine, a lymphokine, a monokine, a stem cell growth factor, a lymphotoxin (LT), a hematopoietic factor, a colony stimulating factor (CSF), an interferon (IFN), parathyroid hormone, thyroxine, insulin, proinsulin, relaxin, prorelaxin, follicle stimulating hormone (FSH), thyroid stimulating hormone (TSH), luteinizing hormone (LH), hepatic growth factor, prostaglandin, fibroblast growth factor, prolactin, placental lactogen, OB protein, a transforming growth factor (TGF), such as TGF-α or TGF-β, insulin-like growth factor (IGF), erythropoietin, thrombopoietin, a tumor necrosis factor (TNF) such as TNF-α or TNF-β, a mullerian-inhibiting substance, mouse gonadotropin-associated peptide, inhibin, activin, vascular endothelial growth factor, integrin, granulocyte-colony stimulating factor (G-CSF), granulocyte macrophage-colony stimulating factor (GM-CSF), an interferon such as interferon-α, interferon-β, or interferon-γ, S1 factor, an interleukin (IL) such as IL-1, IL-1cc, IL-2, IL-3, IL-4, IL-5, IL-6, IL-7, IL-8, IL-9, IL-10, IL-11, IL-12, IL-13, IL-14, IL-15, IL-16, IL-17, IL-18 IL-21 or IL-25, LIF, kit-ligand, FLT-3, angiostatin, thrombospondin, endostatin, and LT. Tumor specific monoclonal antibodies may also be administered in combination with retinoic acid and GTA.

In prophylactic applications, a relatively low dosage may be administered at relatively infrequent intervals over a long period of time. Some patients continue to receive treatment for the rest of their lives. In other therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Compositions can be administered by parenteral, topical, intravenous, intratumoral, oral, subcutaneous, intraarterial, intracranial, intraperitoneal, intranasal or intramuscular means. A typical route of administration is oral, although other routes can be equally effective.

Typically, compositions are prepared as tablets, gel capsules, liquid solutions, suspensions, etc.; solid forms suitable for solution in, or suspension in, liquid vehicles prior to injection can also be prepared. The agents of this invention can be administered in the form of a depot injection or implant preparation which can be formulated in such a manner as to permit a sustained or pulsatile release of the active ingredient. The pharmaceutical compositions are generally formulated as sterile, substantially isotonic and in full compliance with all Good Manufacturing Practice (GMP) regulations of the U.S. Food and Drug Administration.

Toxicity of the combined agents described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition.

The pharmaceutical compositions can be administered in a variety of unit dosage forms depending upon the method of administration. For example, unit dosage forms suitable for oral administration include, but are not limited to, powder, tablets, pills, capsules and lozenges. It is recognized that compositions of the invention when administered orally, should be protected from digestion. This is typically accomplished either by complexing the molecules with a composition to render them resistant to acidic and enzymatic hydrolysis, or by packaging the molecules in an appropriately resistant carrier, such as a liposome or a protection barrier. Means of protecting agents from digestion are well known in the art.

The compositions for administration will commonly comprise an antibody or other ablative agent dissolved in a pharmaceutically acceptable carrier, preferably an aqueous carrier. A variety of aqueous carriers can be used, e.g., buffered saline and the like. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, e.g., sodium acetate, sodium chloride, potassium chloride, calcium chloride, sodium lactate and the like. The concentration of active agent in these formulations can vary widely, and will be selected primarily based on fluid volumes, viscosities, body weight and the like in accordance with the particular mode of administration selected and the patient's needs (e.g., Remington's Pharmaceutical Science (15th ed., 1980) and Goodman & Gillman, The Pharmacological Basis of Therapeutics (Hardman et al., eds., 1996)).

Also within the scope of the invention are kits comprising the active agents and formulations thereof, of the invention and instructions for use. The kit can further contain a least one additional reagent, e.g. a chemotherapeutic drug, ESA, etc. Kits typically include a label indicating the intended use of the contents of the kit. The term label includes any writing, or recorded material supplied on or with the kit, or which otherwise accompanies the kit.

The compositions can be administered for therapeutic treatment. Compositions are administered to a patient in an amount sufficient to substantially ablate targeted cells, as described above. An amount adequate to accomplish this is defined as a "therapeutically effective dose.", which may provide for an improvement in overall survival rates. Single or multiple administrations of the compositions may be administered depending on the dosage and frequency as required and tolerated by the patient. The particular dose required for a treatment will depend upon the medical condition and history of the mammal, as well as other factors such as age, weight, gender, administration route, efficiency, etc.

EXPERIMENTAL

Example 1

Acetate Supplementation Restores Chromatin Accessibility and Tumor Cell Differentiation Using a neuroblastoma differentiation model, we discovered that hypoxia repressed cell differentiation through reducing cellular acetyl-CoA levels, leading to reduction of global histone acetylation and chromatin accessibility. The metabolic switch triggering this global histone hypoacetylation was the induction of pyruvate dehydrogenase kinases (PDK1 and PDK3). Inhibition of PDKs using dichloroacetate (DCA) restored acetyl-CoA generation and histone acetylation under hypoxia. Knocking down PDK1 induced neuroblastoma cell differentiation, highlighting the critical role of PDK1 in cell fate control. Importantly, acetate or glycerol triacetate (GTA) supplementation restored differentiation markers expression and neuron differentiation under hypoxia. Moreover, ATAC-Seq analysis demonstrated that hypoxia treatment significantly reduced chromatin accessibility at RAR/RXR binding sites, which can be restored by acetate supplementation. In addition, hypoxia induced histone hypermethylation by increasing 2-hydroxyglutarate (2HG) and reducing α-ketoglutarate (αKG). αKG supplementation reduced histone hypermethylation upon hypoxia, but did not restore histone acetylation or differentiation markers expression. Together, these findings suggest that diverting pyruvate flux away from acetyl-CoA generation to lactate production is the key mechanism that Warburg effect drives dedifferentiation and tumorigenesis. We propose that combining differentiation therapy with acetate/GTA supplementation might represent an effective therapy against neuroblastoma.

The Warburg effect is a metabolic hallmark of all cancer cells, characterized by increased glucose uptake and glycolysis for lactate generation. The generation and excretion of lactate would appear be a waste of carbon backbone and energy that is needed for proliferation. It was proposed by Warburg that the cause and consequence of the Warburg effect were the injury of respiration and cell dedifferentiation, respectively. However, the connection between impaired respiration and cell dedifferentiation has remained unclear due in part to our limited understanding of metabolism-dependent epigenetic control. How diverting glycolytic carbon away from the TCA cycle promotes tumorigenesis remains incompletely understood. As Warburg pointed out, low oxygen-induced injury to mitochondrial respiration is the origin of the Warburg effect. Hypoxia is a common metabolic stress existing in the tumor microenvironment. Previous studies have showed that hypoxia promotes dedifferentiation of neuroblastoma cells toward a neural crest-like phenotype and favors more aggressive features, which in turn resulting in poor clinical outcome. However, the mechanism by which hypoxia blocks cell differentiation has not been identified.

Neuroblastoma is the most common and deadly pediatric solid tumor, which can arise from neural crest cells that fail to properly exit the cell cycle and differentiate. Unlike many other adult cancer types, neuroblastoma has low exonic mutation frequency even in the high-risk group. Spontaneous regression often occurs in a subset of neuroblastoma patients. The low mutational burden and spontaneous regression that occur in neuroblastoma indicate that reversible epigenetic alterations may play a critical role in regulating neuroblastoma cell differentiation. Retinoic acids induce cell cycle arrest and cell differentiation in neuroblastoma cells, and have been used to treat neuroblastoma as a differentiating agent since the 1980s. However, the efficacy of RA-based differentiation therapy in neuroblastoma patients is less promising when compared to the treatment outcome of acute promyelocytic leukemia patients, especially in high-risk neuroblastoma. The precise mechanism of resistance to differentiation therapy is still not fully understood.

Altered cellular metabolism might remodel the epigenetic landscape to block neuroblastoma cell differentiation under hypoxia. Confirming this hypothesis, it is shown herein that hypoxia suppressed the RA-induced neuroblastoma cell differentiation and the expression of differentiation markers. Neuroblastoma cells exposed to hypoxia exhibited enhanced glycolysis and impaired oxidative phosphorylation, resulting in a significant decrease in both acetyl-CoA and histone acetylation levels. These metabolic changes were associated with hypoxic induction of pyruvate dehydrogenase kinases (PDK1 and PDK3). Inhibition of PDKs by dichloroacetate (DCA) restored histone acetylation under hypoxia. Importantly, acetate supplementation restored histone acetylation, chromatin accessibility, neuron differentiation markers expression and neuron differentiation morphology. Together, these findings demonstrate that (1) combining RA-based differentiation therapy and acetate supplementation provides an effective therapeutic strategy for neuroblastoma treatment; (2) diverting pyruvate away from acetyl-CoA generation is a key mechanism by which the Warburg effect blocks cell differentiation to promote tumorigenesis.

Hypoxia represses RA-induced neuron differentiation marker expression. To test Warburg's hypothesis that injury of respiration causes cell dedifferentiation, two neuroblastoma cell lines, CHP134 and SMS-KCNR, were treated with 10 µM 13-cis-retinoic acid (RA) under normoxia (21% O2) or hypoxia (0.5% O2). After 48 h under normoxia, RA treatment induced obvious cell morphological changes to a mature neuronal-like phenotype characterized by neurite outgrowth, while hypoxia partially diminished nerite outgrowth and the differentiation morphology (FIGS. 1A and B). Thus, these data indicate CHP134 and SMS-KCNR neuroblastoma cells are appropriate models to investigate the mechanism of differentiation resistance under hypoxia.

Figure 9:
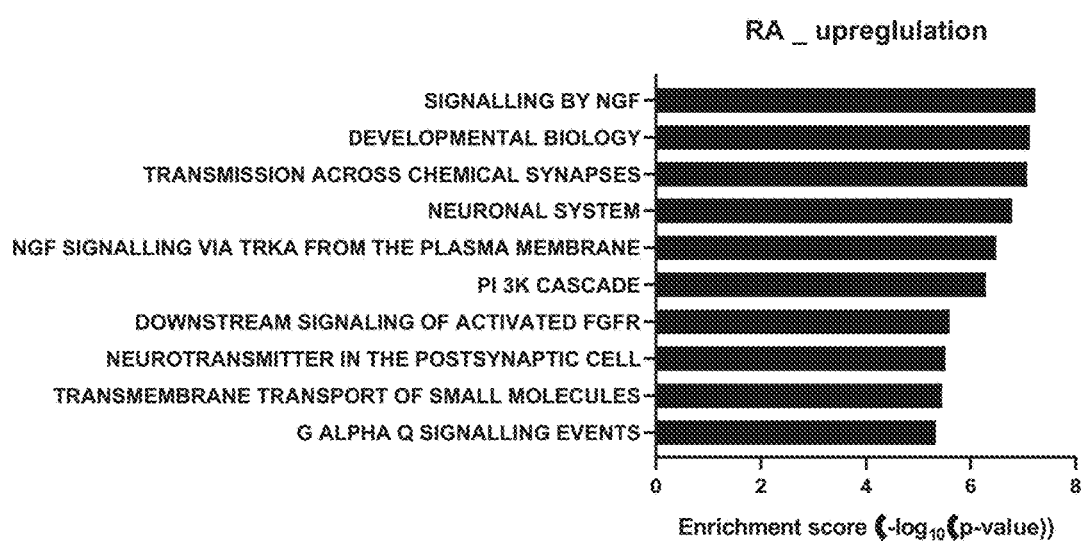
FIG. 9. Pathway enrichment of genes which were induced by RA treatment.

Differentiation is determined by expressing specific differentiation markers. To identify neuron-specific differentiation markers that are induced by RA treatment but suppressed by hypoxia, we performed RNA-Seq analysis to determine transcripts abundance after 24 h RA or DMSO treatment under normoxia or hypoxia. Pathway analysis of RA-upregulated genes indicated the enrichment of NGF signaling, transmission across of chemical synapses and neuronal system genes by RA treatment (FIG. 9). We hypothesize that genes that are involved in neuroblastoma differentiation will be induced by RA treatment under normoxia but not under hypoxia. Following this criterion, we identified a group of genes as potential neuron-specific markers (FIG. 1C). Two representative differentiation markers are nerve growth factor receptor (NGFR) and synuclein gamma (SNCG) among others (FIG. 1D). It was reported that NGFR was down-regulated by MYCN amplification to maintain an undifferentiated and more aggressive phenotype. SNCG is traditionally characterized as a neuronal marker which is highly expressed in peripheral sensory neurons. Using a public data set from the R2 Genomics Analysis and Visualization Platform, we found that higher expression of NGFR and SNCG associated with a better overall survival rate (FIG. 1E). Moreover, the expression of NGFR and SNCG was negatively correlated with the expression of hypoxia marker PDK1 (FIG. 1F). Altogether, our results indicate that the expression of these neuronal differentiation markers is repressed under hypoxia, and the hypoxic tumor microenvironment may present a challenge to the efficacy of differentiation therapy in the treatment of neuroblastoma.

Figure 2:
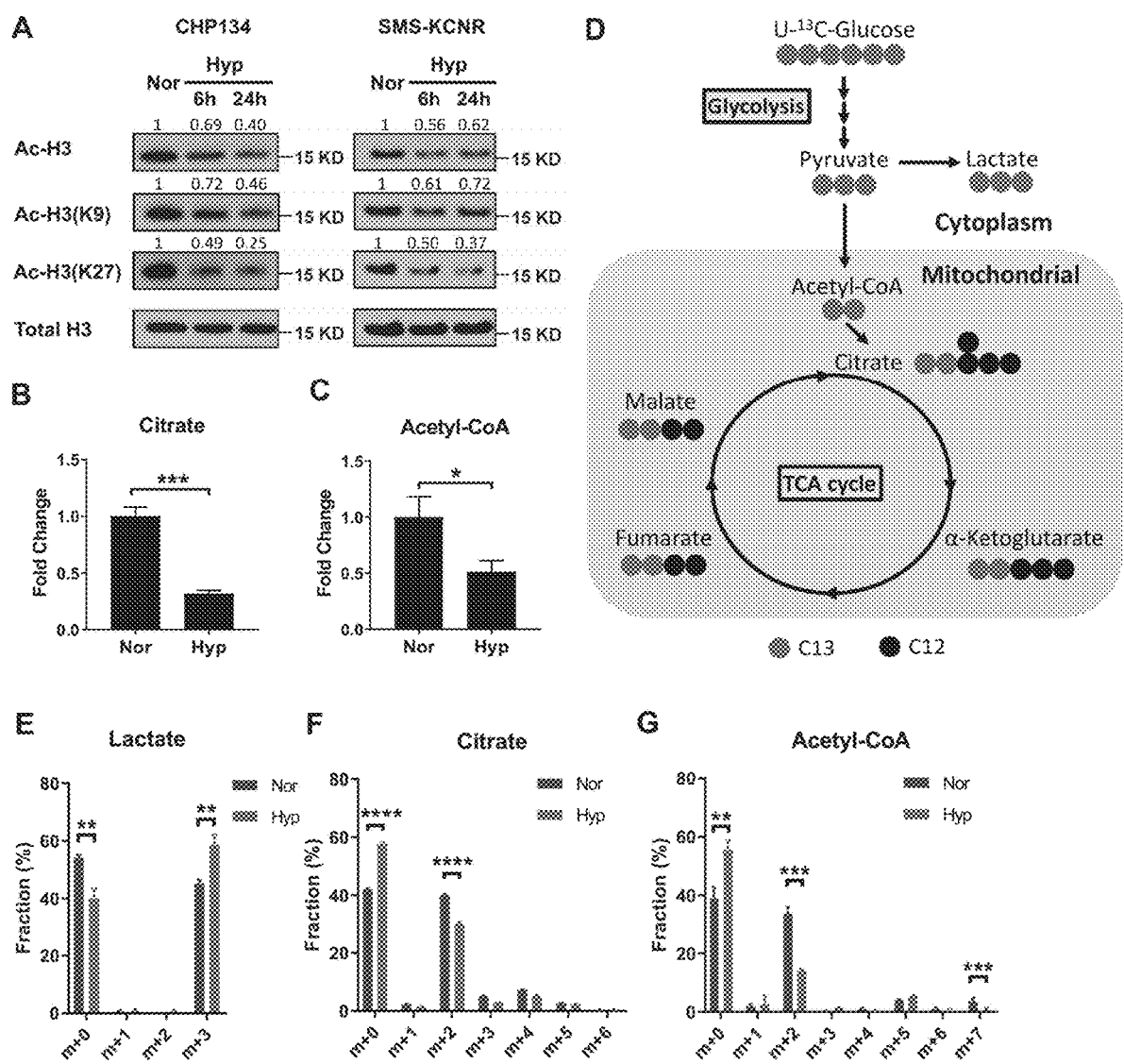
FIG. 2. Hypoxia causes histone hypoacetylation by decreasing citrate and acetyl-CoA generation. (A) Time course study of acetylation on H3K9, H3K27, and total H3 in CHP134 and SMS-KCNR cells under hypoxia by immunoblots. The band intensity was quantified with Imagelab 6.0.1 software (Bio-Rad) and normalized to loading control. (B, C) Both citrate and acetyl-CoA levels were measured using LC-MS (n=3). (D) Schematic of labelling patterns of U-$^{13}$C-glucose flux through metabolic pathways. (E-G) Isotopomer distribution of lactate, citrate and acetyl-CoA from CHP134 cells cultured in the presence of U-$^{13}$C glucose for 3 h with or without 16 h hypoxia pretreatment (n=3). (Data in B-C and E-G are represented as mean±SD of three biological repeats. * P<0.05;  P<0.01; * P<0.001, determined by Student's two-tailed t-test.)
Figure 10:
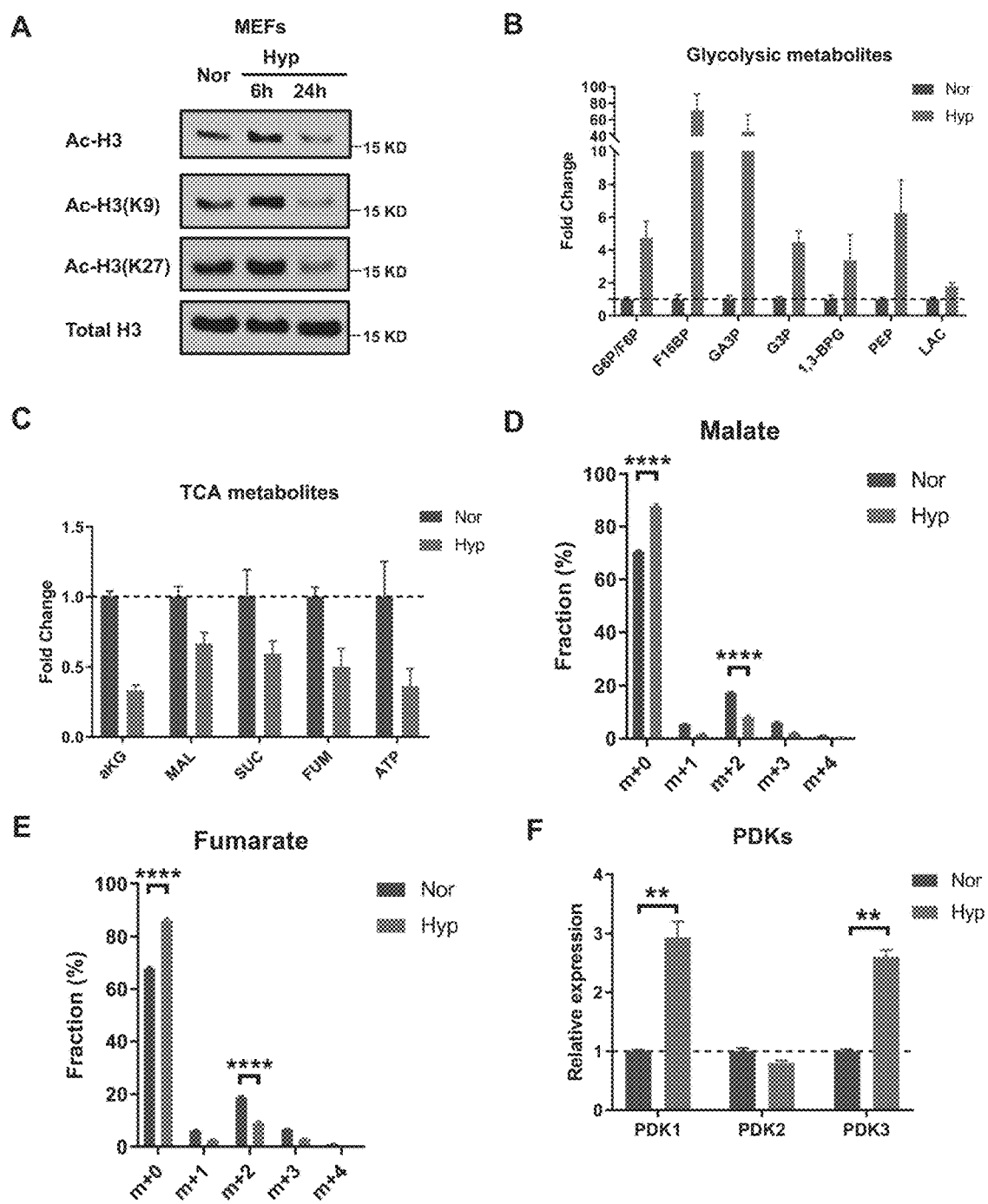
FIG. 10. Hypoxia reprograms cellular metabolism. (A) Time course study of acetylation on H3K9, H3K27, and totalH3 in MEFs under hypoxia. (B) Measurement of glycolytic intermediates by LC-MS after 24 h hypoxia treatment in CHP134 cells. (C) Measurement of TCA cycle intermediates by LC-MS after 24 h hypoxia treatment in CHP134 cells. (D-E) Isotopomer distribution of malate and fumarate from CHP134 cells cultured in the presence of U-13 C glucose for 3 h under normoxia or hypoxia.(F) PDK1/2/3 expression by RNA-Seq analysis after 24 h hypoxia treatment in CHP134 cells. (Data in B-F are represented as mean±SO of three biological repeats. * P<0.05;  P<0.01; * P<0.001, **** P<0.0001 determined by Student's two-tailed t-test.)

Hypoxia induces histone hypoacetylation by reducing acetyl-CoA and citrate generation. RA is the ligand of nuclear retinoid and rexinoid receptors (RAR and RXR). Activation of RA-dependent transcriptional signaling requires histone acetyltransferases (HATs) to acetylate histone, leading to chromatin remodeling over target gene promoters. Given that HATs activity is required for RA-induced differentiation, we next explored whether hypoxia regulated chromatin accessibility through changing histone acetylation status. We observed that acetylation of histone H3K9, H3K27, and total H3 acetylation were significantly decreased under hypoxia in both CHP134 and SMS-KCNR cells (FIG. 2A), indicating that histone acetylation levels were controlled by oxygen availability. In mouse embryonic fibroblasts (MEFs), a non-tumorigenic cell line, we observed hypoxia treatment increased histone acetylation at 6 h, but significantly decreased histone acetylation at 24 h (FIG. 10A). HATs require acetyl-CoA as substrate in the acetylation reaction. Cytosolic pyruvate can be transported into mitochondria and converted to acetyl-CoA through pyruvate dehydrogenase (PDH). Mitochondrial acetyl-CoA is then combined with oxaloacetate to produce citrate in a reaction that is catalyzed by citrate synthase. Importantly, acetyl-CoA cannot cross the mitochondrial membrane, while citrate can be transported across mitochondrial membrane, meaning that mitochondrial acetyl-CoA must first be converted to citrate before it can contribute to the cytosolic pool of acetyl-CoA. In cytosol, citrate is the major source of acetyl-CoA production through a reaction catalyzed by ATP citrate lyase (ACLY). To investigate whether hypoxia regulates cellular acetyl-CoA and citrate levels, CHP134 cells were cultured under normoxia or hypoxia, and their intracellular metabolites were extracted and profiled by liquid chromatography—mass spectrometry (LC-MS). Notably, a significant increase in glycolytic intermediates and lactate was observed in hypoxic cells, confirming the enhanced Warburg effect under hypoxia (FIG. 10B). We also found that both acetyl-CoA and citrate levels decreased after 24 h of hypoxia treatment, suggesting that hypoxia treatment downregulated total intracellular acetyl-CoA and citrate (FIGS. 2B and C). Other TCA intermediates including α-ketoglutarate, succinate, malate, and fumarate also decreased after 24 h of hypoxia treatment (FIG. 10C).

To determine whether the reduction of acetyl-CoA and citrate under hypoxia is caused by decreased pyruvate flux entering the TCA cycle, we performed an isotope tracing study using U-$^{13}$C-Glucose as a tracer and profiled the mass isotopomer distribution of the downstream metabolites by high-resolution LC-MS (FIG. 2D). A mass isotopomer distribution is a profile containing the relative abundances of each successive mass isotopomer (i.e., M+0, M+1, M+2, and so on). After correction of natural isotope distribution, the specific distribution of stable isotope labelled precursors into metabolic products can be used to represent the metabolic dynamics/flux through the metabolic networks. Consistent with targeted metabolomics analysis, hypoxia treatment resulted in a lower labeling fraction of TCA intermediates including malate [M+2], fumarate [M+2], and citrate [M+2], but higher labeling fraction of lactate [M+3] (FIGS. 2E and F, Supplemental Figure S2D and E). Acetyl-CoA can be labeled by U-$^{13}$C-Glucose at the acetyl group, ribose group or both, which reflected by mass shifts of [M+2], [M+5] or [M+7] respectively. We found the labeling fraction of acetyl-CoA [M+2] and [M+7] were both decreased under hypoxia (FIG. 2G), indicating that carbon flux into the acetyl-CoA pool through pyruvate was reduced. Altogether, these results suggest that reduction of citrate and acetyl-CoA levels under hypoxia is due to decreased pyruvate flux entering the TCA cycle.

Figure 3:
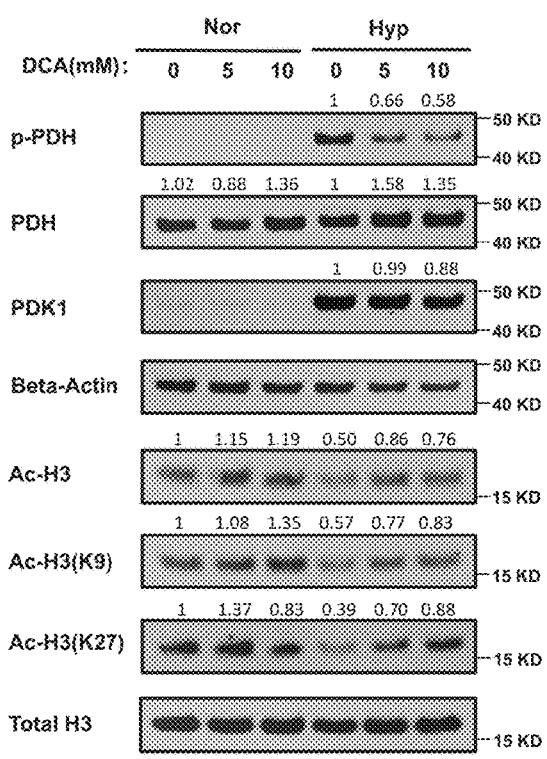
FIG. 3. DCA restores pyruvate flux into TCA cycle and histone acetylation. (A) Immunoblots of p-PDH, total PDH, PDK1, beta-Actin, acetylation on H3K9, H3K27 and total H3 under normoxia or hypoxia treated with DMSO, 5 mM or 10 mM DCA. (B, C) Isotopomer distribution of citrate and acetyl-CoA from CHP134 cells cultured in the presence of U-$^{13}$C glucose for 3 h under normoxia, hypoxia, or hypoxia with 5 mM DCA treatment. (Data in B and C are represented as mean±SD of three biological repeats. * P<0.05;  P<0.01; * P<0.001, determined by Student's two-tailed t-test.) (D) CHP134 cells were infected with lentivirus expressing shRNA targeting PDK1 or PDK3 (three independent vectors). After puromycin selection, representative images from each pool population were shown. (E) Quantification of neurite outgrowth in (D)
Figure 3:
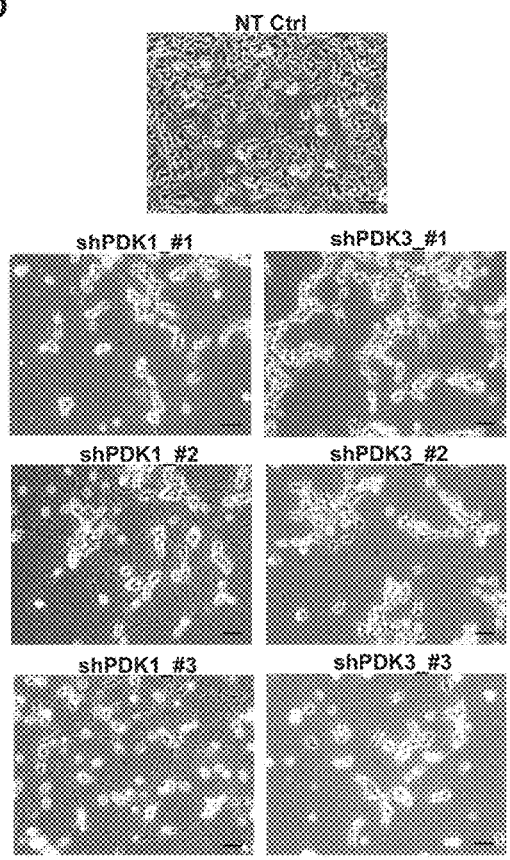
Figure 3:
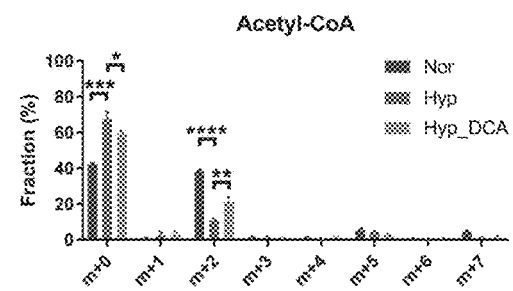
Figure 3:
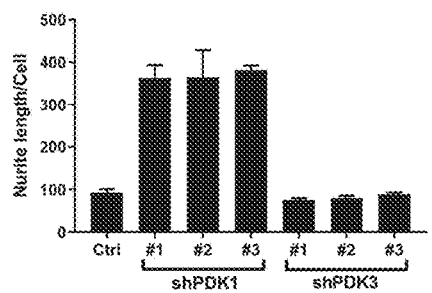
Figure 3:
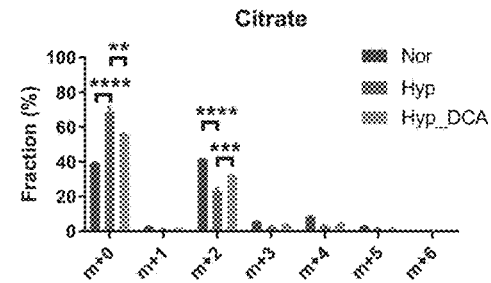

Inhibition of PDKs activity restores pyruvate flux into TCA cycle and histone acetylation. We next explored the molecular mechanism by which hypoxia reduces acetyl-CoA generation. The pyruvate dehydrogenase (PDH) complex is the key enzyme that controls the pyruvate entry into the TCA cycle by converting pyruvate to acetyl-CoA. It has been previously reported that hypoxia-inducible factor-1 (HIF-1) induces the expression of PDK1 and PDK3 which then phosphorylate and inhibit PDH to reduce pyruvate entry into the TCA cycle. This reduces reactive oxygen species levels and protects cells under stress condition. Thus, PDK is critical in regulating oxidative phosphorylation and the intracellular levels of TCA intermediates including citrate, which could potentially regulates histone acetylation status. PDK1 and PDK3 induction under hypoxia in CHP134 cells was validated by our RNA-Seq data (FIG. 10F). Under hypoxia, PDK1 protein level was significantly increased, associated with elevated PDH phosphorylation (FIG. 3A). To determine whether PDK induction under hypoxia is responsible for reduction of histone acetylation, we tested whether dichloroacetate (DCA), an inhibitor of PDKs, could restore histone acetylation by promoting acetyl-CoA production. Our results showed that DCA treatment inhibited PDK1 activity and decreased PDH phosphorylation under hypoxia (FIG. 3A). While DCA treatment slightly increased acetylation of H3K9 and total acetyl-H3 under normoxia, the acetylation restoration effect was much more pronounced under hypoxia. In particular, DCA treatment restored H3K27 acetylation in a dose-dependent manner under hypoxia (FIG. 3A). In addition, isotope tracing study further confirmed that DCA treatment under hypoxia increased labeling fraction of acetyl-CoA [M+2] and citrate [M+2], indicating that PDH activity had been partially rescued (FIGS. 3B and C). Taken together, our results indicate that PDK inhibition restores histone acetylation under hypoxia by increasing the flux of pyruvate entry into the TCA cycle through the PDH complex. Next, we tested whether knocking down PDK1 or PDK3 could induce cell differentiation. Intriguingly, all three shRNA vectors targeting PDK1 caused significantly cell death in CHP134 cells after puromycin selection, the cells survived displayed neuron differentiation morphology and stopped proliferating (FIGS. 3D and E). In contrast, all three shRNA vectors targeting PDK3 only reduced cell proliferation but did not induce neuron differentiation morphology (FIGS. 3D and E), suggesting a critical role of PDK1 in regulating neuroblastoma cell differentiation.

Figure 4:
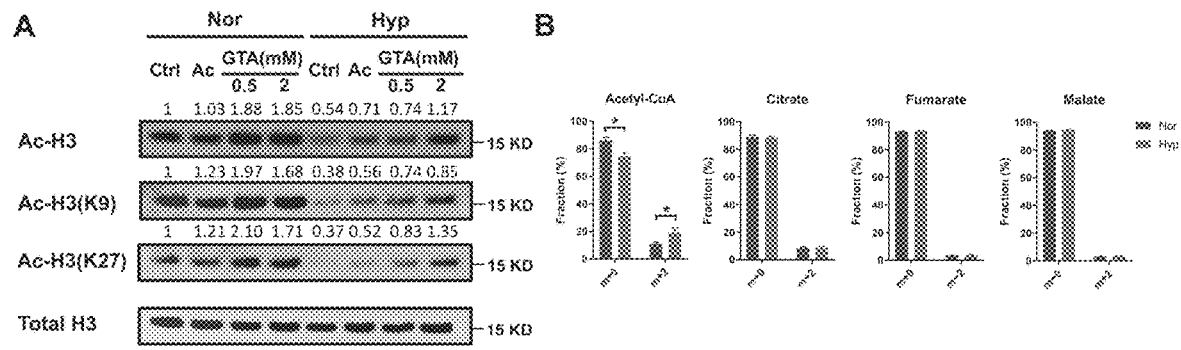
FIG. 4. Acetate supplementation increases the expression of differentiation markers by promoting histone acetylation. (A) Immunoblots of acetylation on H3K9, H3K27, and total H3 under normoxia or hypoxia treated with vehicle control, 5 mM acetate, 0.5 mM GTA or 2 mM GTA. (B) Isotopomer distribution of acetyl-CoA, citrate, fumarate and malate from CHP134 cells cultured in the presence of U-$^{13}$C acetate for 3 h with or without 16 h hypoxia pretreatment. (C and D) qPCR analysis for SNCG and NGFR expression in CHP134 cells treated with DMSO, 10 μM RA alone, or 10 μM RA combined with 5 mM acetate or 2 mM GTA for 16 h under normoxia or hypoxia. (E) Model of histone acetylation and cell differentiation regulation under hypoxia. (Data in B represent mean±SD of three biological repeats. Data in C and D are represented as mean±SD of triplicate PCR reactions; a representative of two independent experiments is shown. * P<0.05;  P<0.01; * P<0.001, **** P<0.0001, determined by Student's two-tailed t-test.)
Figure 4:
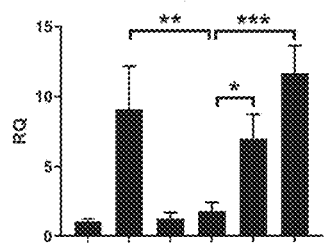
Figure 4:
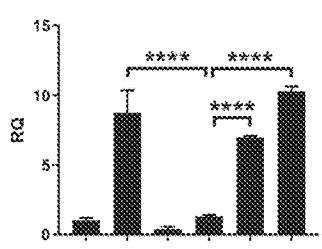
Figure 4:
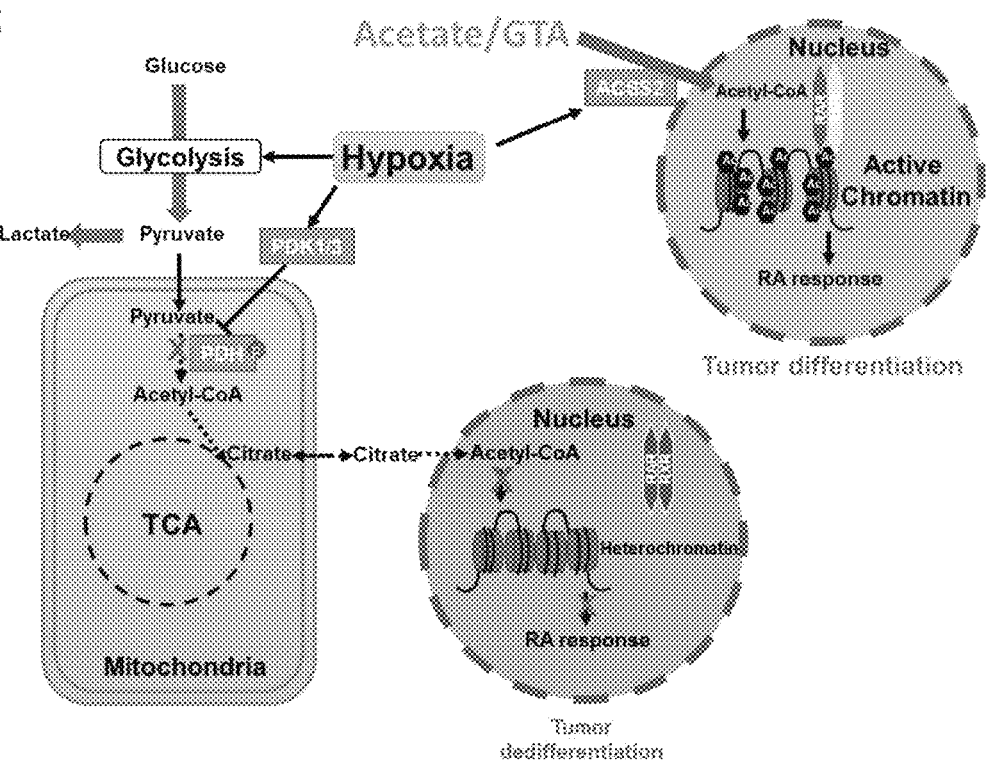

Acetate supplementation restores histone acetylation and promotes RA-induced differentiation. Acetate can supplement the cellular acetyl-CoA pool though Acetyl-CoA synthetases (ACSS1/2/3). ACSS1 and ACSS3 localize to mitochondria, converting acetate to acetyl-CoA for ATP production, while ACSS2 localizes to cytoplasm and contributes to the cytosolic and nuclear acetyl-CoA pool. Interestingly, it was shown that ACSS2 was necessary for neuronal genes expression and memory formation. Since we observed that hypoxia prevented RA-induced differentiation of neuroblastoma cells and this lack of differentiation was associated with histone H3 hypoacetylation and a depletion of acetyl-CoA, we reasoned that replenishing acetyl-CoA level with acetate supplementation would restore histone acetylation and RA-induced differentiation under hypoxia. Consistent to a previous report that hypoxia induces ACSS2, our RNA-Seq data indicated that hypoxia specifically induced the expression of cytosolic ACSS2, but not mitochondrial ACSS1 and ACSS3 (FIG. 11A), giving further support for the potential of acetate supplementation to increase acetyl-CoA levels under hypoxia. To test this hypothesis, CHP134 cells were supplemented with 5 mM acetate, 0.5 mM or 2 mM glycerol triacetate (GTA). GTA is a short-chain triglyceride that can release three molecular equivalents of acetate per molecule of GTA and has been proven as an effective acetate precursor. FDA has approved GTA as a food additive for infants with Canavan disease, since GTA treatment had no detectable toxicity even when using high dose. In our study, both acetate and GTA treatment restored acetylation on H3K9, H3K27, and total H3 under hypoxia (FIG. 4A). To explore how acetate is utilized by the cells, we performed a tracing study with U-$^{13}$C-acetate as a tracer. We observed the percentage of $^{13}$C labeled citrate[M+2], malate[M+2] and fumarate [M+2] was similar between normoxia and hypoxia. However, hypoxia treatment led to a higher fraction of $^{13}$C labeled acetyl-CoA [M+2] than normoxia (FIG. 4B), indicating acetate supplementation can promote cellular acetyl-CoA production under hypoxia.

Figure 11:
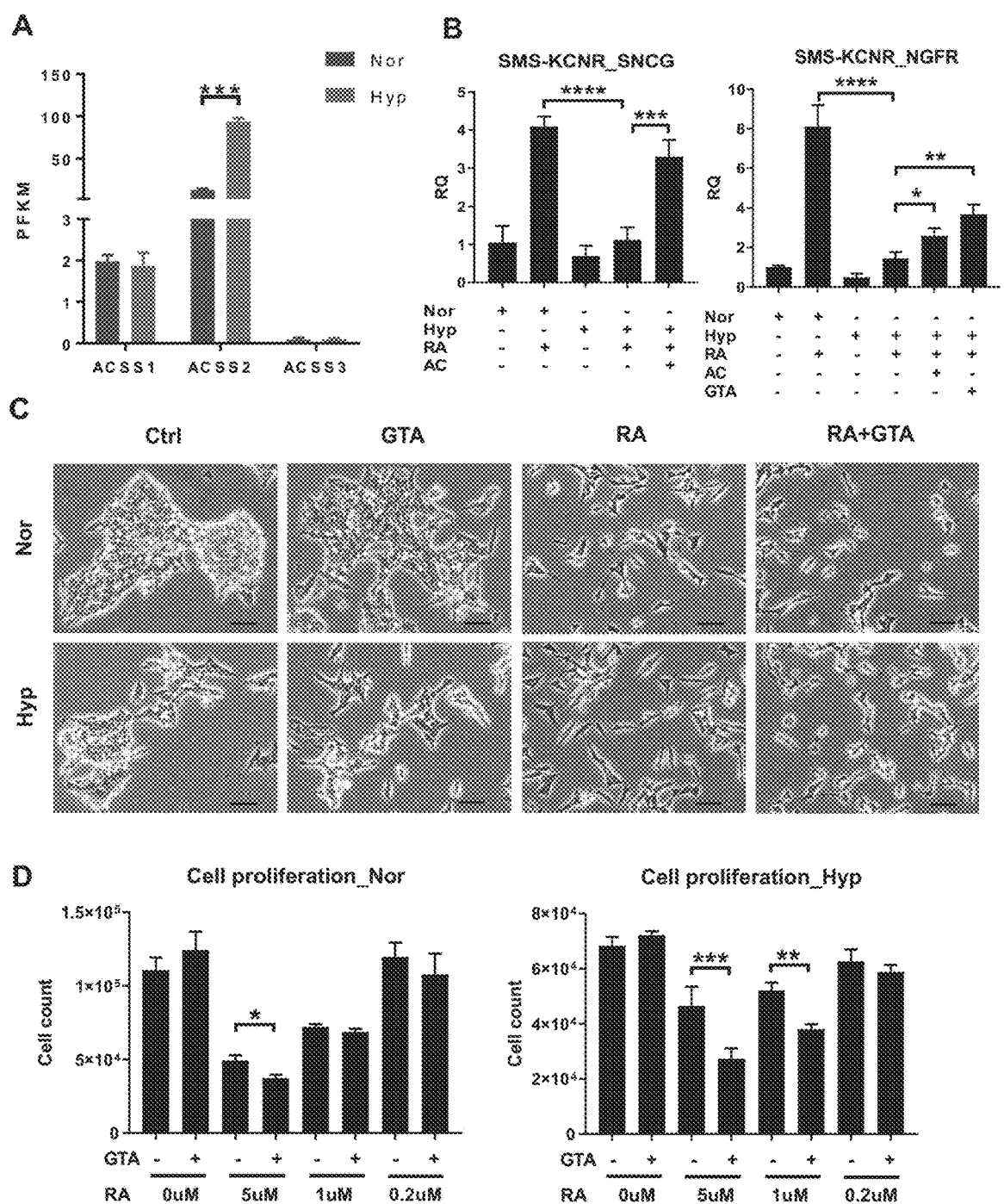
FIG. 11. Acetate supplementation restores RA-induced cell differentiation under hypoxia. (A) ACSS1/2/3 expression by RNA-Seq analysis after 24 h hypoxia treatment in CHP134 cells. (B) qPCR analysis for SNCG and NGFR expression in SMS-KCNR cells treated with DMSO, 101JM RA alone, 101JM RA combined with 5 mM acetate or 2 mM GTA for 16 h under normoxia or hypoxia. (C) SMS-KCNR cell differentiation induced by 101JM RA, 2 mM GTA, or 101JM RA plus 2 mM GTA for 48 h under normoxia or hypoxia. (D) CHP134 cell proliferation measured in 24 well-plate after treatment with DMSO, 0.2 uM, 1 uM, or 51JM RA plus 2 mM GTA under normoxia or hypoxia for 48 h. (Data in A and 0 are represented as mean±SO of three biological repeats. Data in B are represented as mean±SO of triplicate PCR reactions; a representative of two independent experiments is shown. * P<0.05;  P<0.01; * P<0.001, **** P<0.0001 determined by Student's two-tailed t-test.)

Next, we investigated whether acetate supplementation could restore the expression of differentiation markers under hypoxia. CHP134 cells were cultured under normoxia or hypoxia for 16 h, then RA and/or acetate/GTA were added to each group to determine the effect of acetate supplementation on RA-induced cell differentiation. Supporting our hypothesis that acetate supplementation could promote differentiation therapy, the results showed that acetate or GTA treatment significantly restored the expression of NGFR and SNCG under hypoxia in both CHP134 and SMS-KCNR cells (FIGS. 4C and D, FIG. 11B). The regulatory model of histone acetylation and cell differentiation under hypoxia was illustrated in FIG. 4E. Acetate supplementation restores cellular acetyl-CoA pool and histone acetylation under hypoxia, which in turn increases chromatin accessibility and promotes transcriptions of RA response genes.

Figure 5:
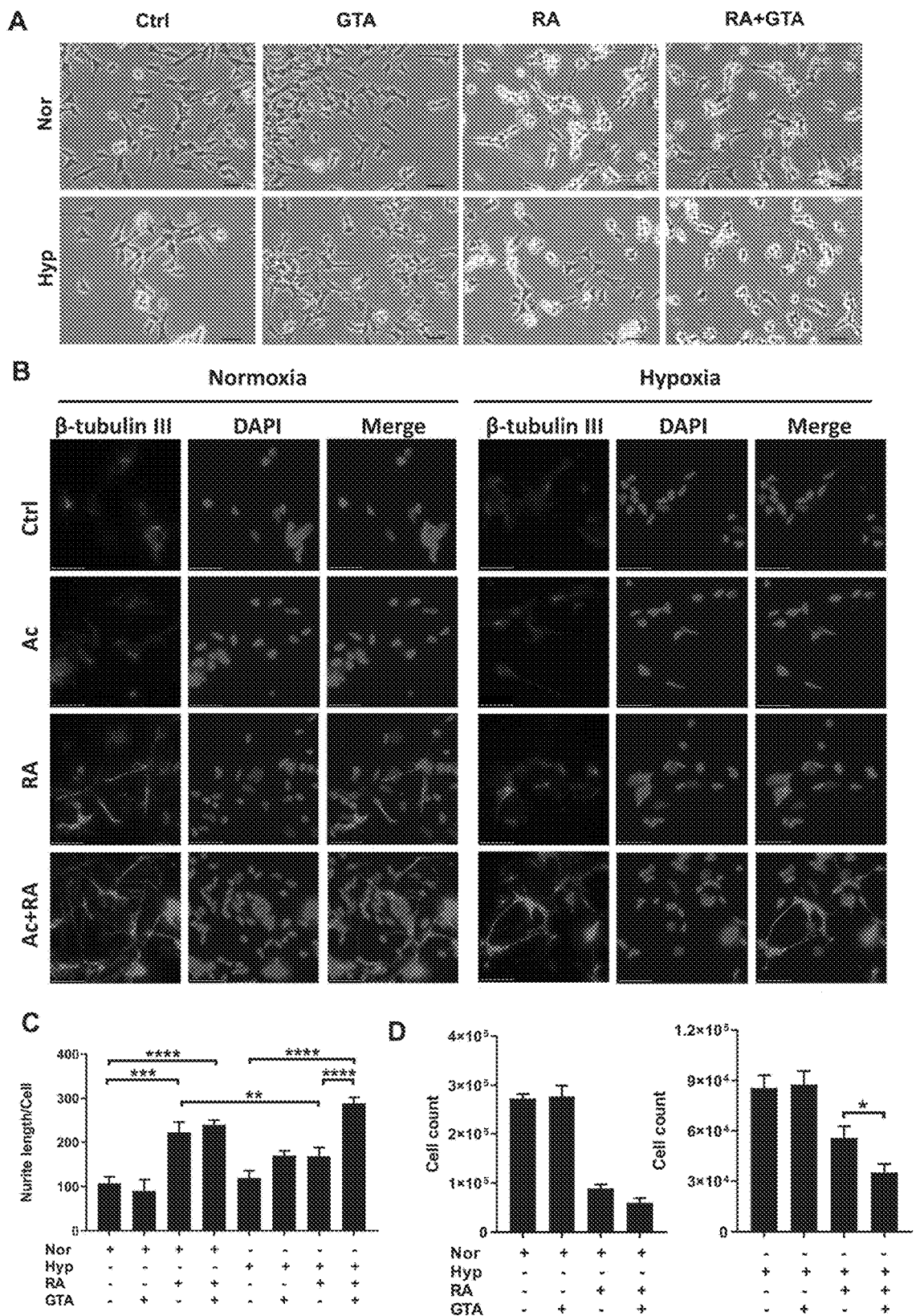
FIG. 5. Acetate supplementation restores neuroblastoma cell differentiation under hypoxia. (A) CHP134 cell differentiation induced by 10 μM RA, 2 mM GTA, or 10 μM RA plus 2 mM GTA for 48 h under normoxia or hypoxia. Scale bar: 50 μm. (B) Immunofluorescence staining of β-tubulin III and DAPI in CHP134 cells treated with 10 μM RA, 5 mM acetate, or 10 μM RA plus 5 mM acetate for 72 h under normoxia or hypoxia. Scale bar: 50 μm. (C) Quantification of neurite outgrowth in (A). (D) CHP134 cell proliferation measured in 12 well-plate treated with 10 μM RA, 2 mM GTA, or 10 μM RA plus 2 mM GTA under normoxia or hypoxia for 48 h. (Data in C and D are represented as mean±SD of three biological repeats. * P<0.05;  P<0.01; * P<0.001, **** P<0.0001, determined by Student's two-tailed t-test.)
Figure 12:
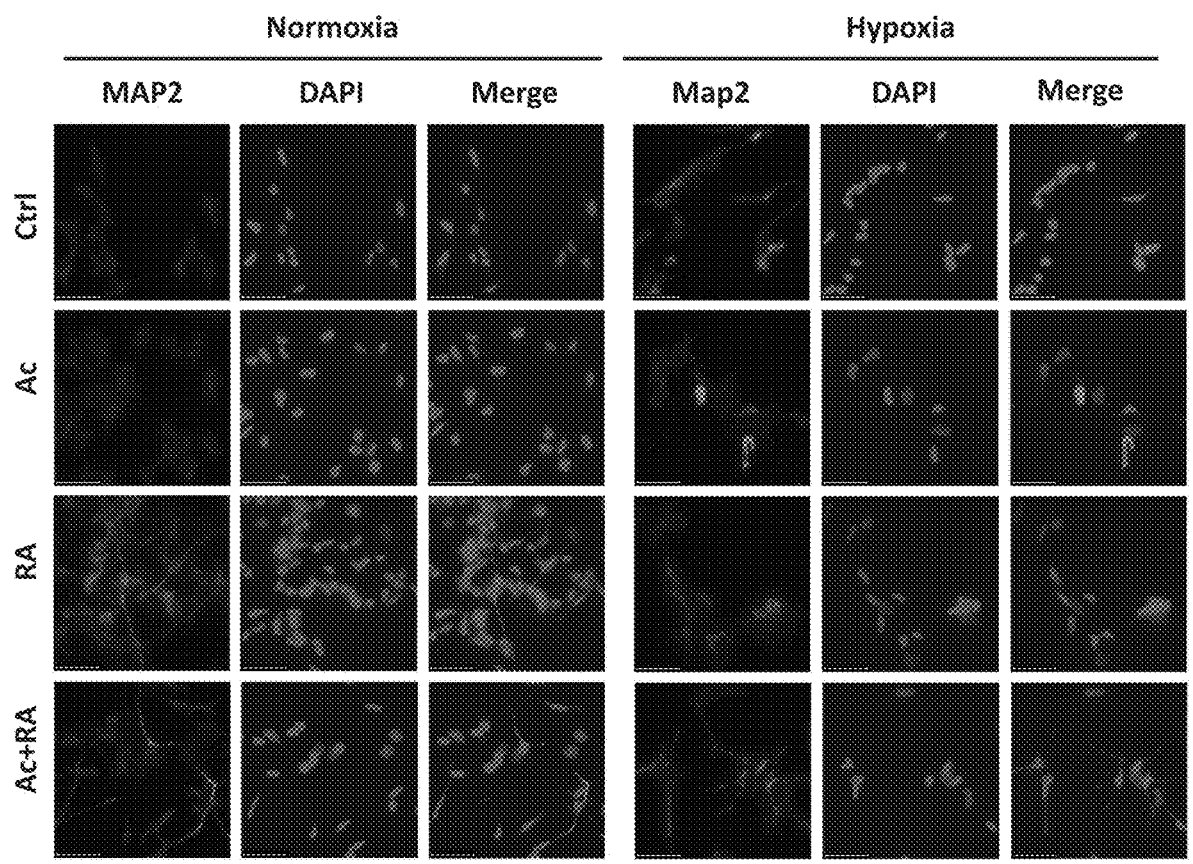
FIG. 12. Immunofluorescence staining of MAP2 and DAPI in CHP134 cells treated with 101JM RA, 5 mM acetate, or 101JM RA plus 5 mM acetate for 72 h under normoxia or hypoxia.

Additionally, GTA supplementation restored the RA-induced neuron-like morphological changes in both CHP134 and SMS-KCNR cells under hypoxia (FIGS. 5A and C, Supplemental Figure S3 C). Neuroblastoma differentiation was further confirmed by immunofluorescence staining against neuron specific β-tubulin III (Tuj1) and microtubule associated protein 2 (MAP2). RA treatment induced neuronal morphological changes, demonstrated by increased β-tubulin III/MAP2 positive neurites under normoxia, which was partially suppressed under hypoxia. Combination of RA and acetate treatment could restore neuronal differentiation under hypoxia (FIG. 5B and FIG. 12). Moreover, combination of RA and GTA re-sensitized CHP134 cells to RA-induced proliferation arrest under hypoxia (FIG. 5D and FIG. 11D).

Figure 6:
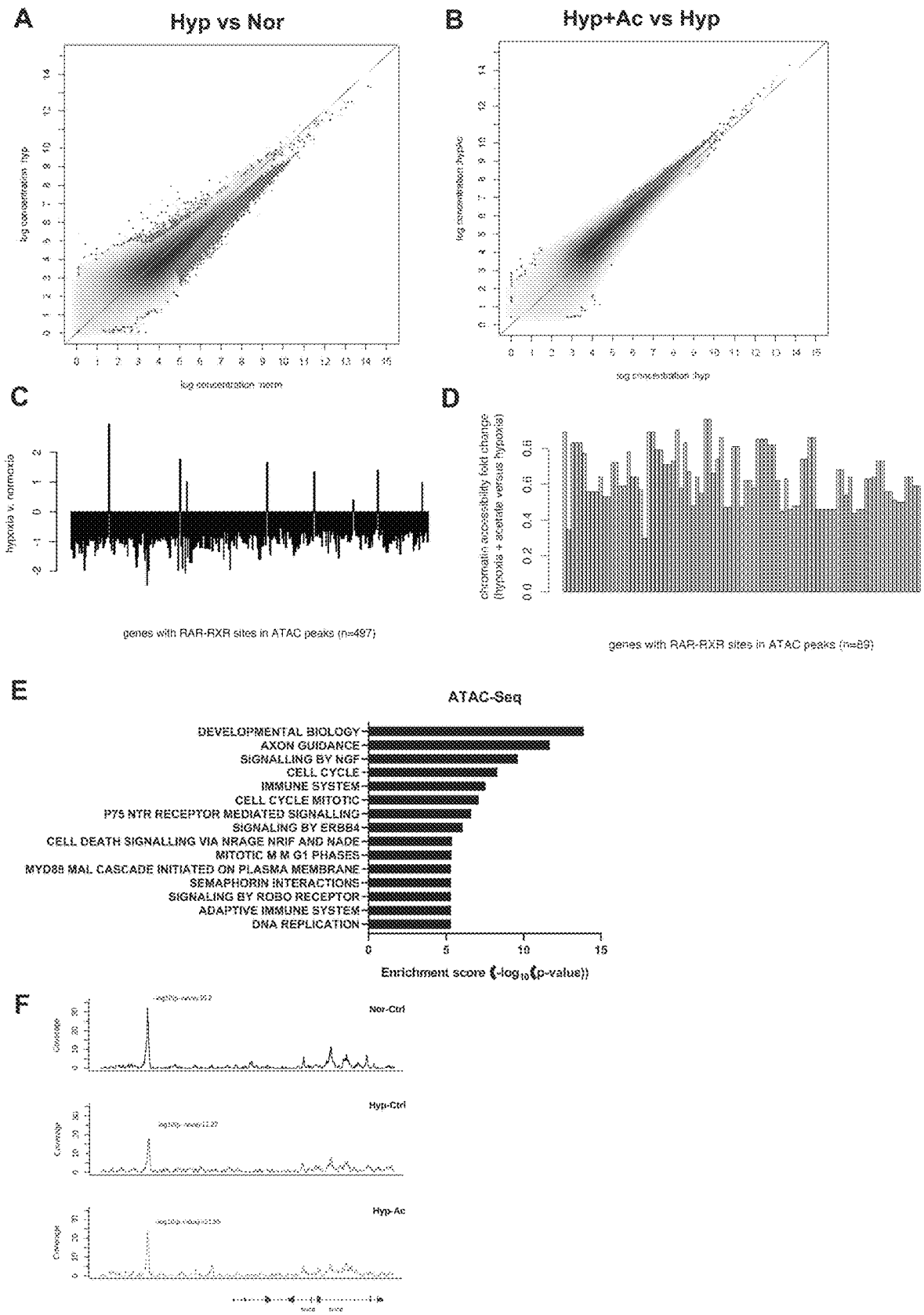
FIG. 6. ATAC-Seq reveals that chromatin accessibility of RAR-RXR target genes and differentiation markers are restored by acetate supplementation under hypoxia (A) Comparison of chromatin accessibility under normoxia and hypoxia. (B) Chromatin accessibility changes in response to acetate supplementation under hypoxia. (C) Genes with RAR-RXR binding site showed decreased chromatin accessibility under hypoxia. (D) Acetate supplementation increased chromatin accessibility of genes with RAR-RXR sites under hypoxia. (E) Pathway enrichment of genes whose chromatin accessibility was decreased under hypoxia and restored by acetate supplementation. (F) Browser track of SNCG under normoxia, hypoxia and hypoxia with 5 mM acetate.

ATAC-Seq analysis reveals that acetate supplementation restores chromatin accessibility at RAR/RXR binding sites upon hypoxia. We employed ATAC-Seq to investigate the effect of hypoxia and acetate supplementation on chromatin accessibility. Our data indicated hypoxia treatment resulted in a more condensed chromatin structure, while acetate partially restored chromatin accessibility (FIGS. 6A and B). Further analysis of genes with RAR/RXR binding sites showed decreased chromatin accessibility of these loci under hypoxia and increased chromatin accessibility by acetate treatment (FIGS. 6C and D). Interestingly, pathway analysis demonstrated the genes whose chromatin accessibility was decreased under hypoxia and restored by acetate supplementation were enriched in development biology, axon guidance, signaling by NGF and p75 neurotrophin receptor (NTR) (FIG. 6E). The track of one representative neuron differentiation marker SNCG was shown in FIG. 6F. At upstream of SNCG gene, we identified a peak whose coverage was reduced under hypoxia but restored upon acetate supplementation.

Figure 7:
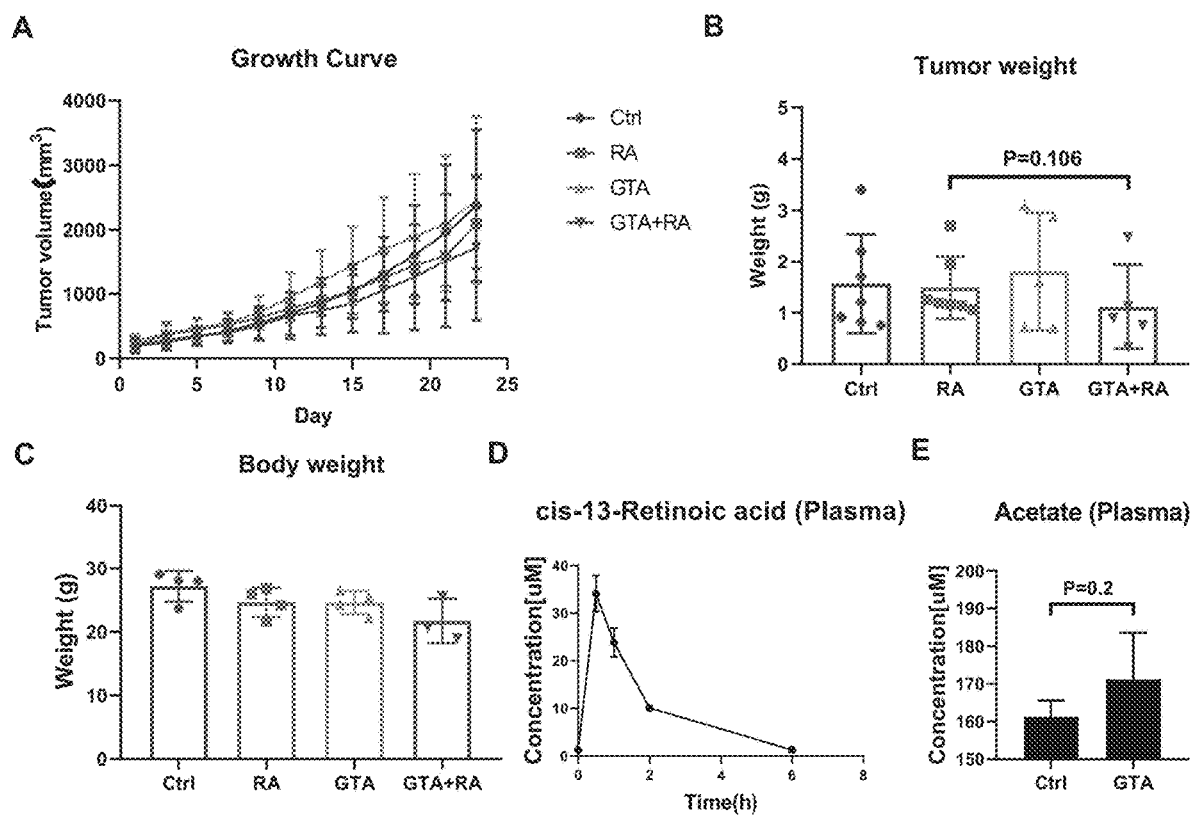
FIG. 7. In vivo xenograft study in NSG mice. (A) Tumor volume of CHP134 mice xenografts as measured every other day. NSG mice xenografted with CHP134 cells were randomized into 4 groups and received 10 mg/kg RA via i.p. injection, 5% GTA in drinking water or both. (B) Tumor weights at experimental endpoint. (Control group: n=7, RA group: n=7, GTA group: n=5 and GTA+RA group: n=5). (C) Body weights at experimental endpoint. (Control group: n=4, RA group: n=4, GTA group: n=4 and GTA+RA group: n=3, one mouse died during treatment). (D) Pharmacokinetics of RA in NSG mice following administration of 10 mg/kg RA via i.p. injection. Plasma samples at each time point were collected from tail vein (n=3). (E) Acetate measurement in the plasma of NSG mice in control and GTA group (n=3). (Results in A-E are represented as mean±SD.)
Figure 8:
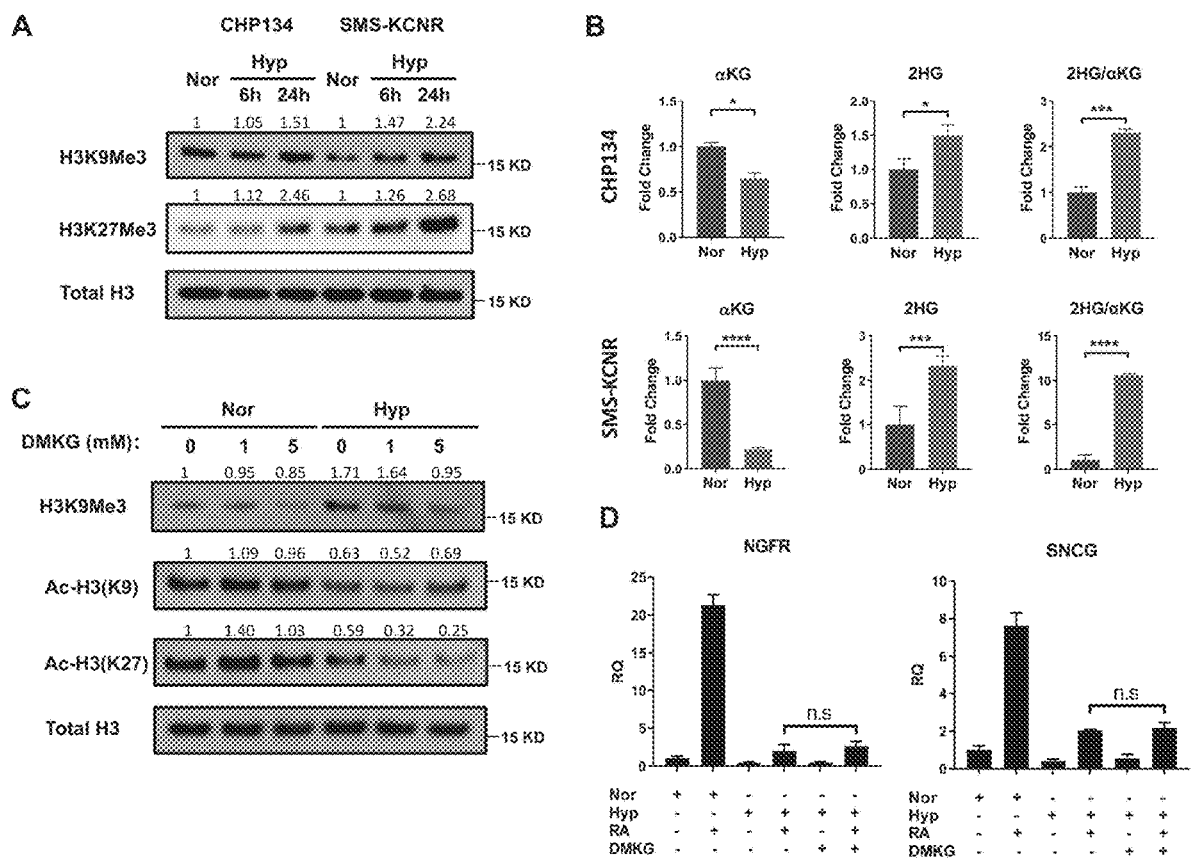
FIG. 8. αKG reduces hypoxia-induced histone hypermethylation, but cannot restore the expression of differentiation markers. (A) Time course study of tri-methylation on H3K9, H3K27 in CHP134 and SMS-KCNR cells under hypoxia. (B) Hypoxia decreased αKG level, but increased 2HG production and 2HG/αKG ratio in CHP134 and SMS-KCNR cells. (C) Immunoblots of histone methylation and acetylation markers under normoxia or hypoxia treated with vehicle control, 1 mM or 5 mM DMKG in CHP134 cells. (D) qPCR analysis for SNCG and NGFR expression in CHP134 cells treated with DMSO, 10 μM RA alone, 5 mM DMKG alone or 10 μM RA combined with 5 mM DMKG for 16 h under normoxia or hypoxia. (Data in B are represented as mean±SD of three biological repeats. Data in D are represented as mean±SD of triplicate PCR reactions; a representative of two independent experiments is shown. * P<0.05;  P<0.01; * P<0.001, **** P<0.001, determined by Student's two-tailed t-test.)
Figure 13:
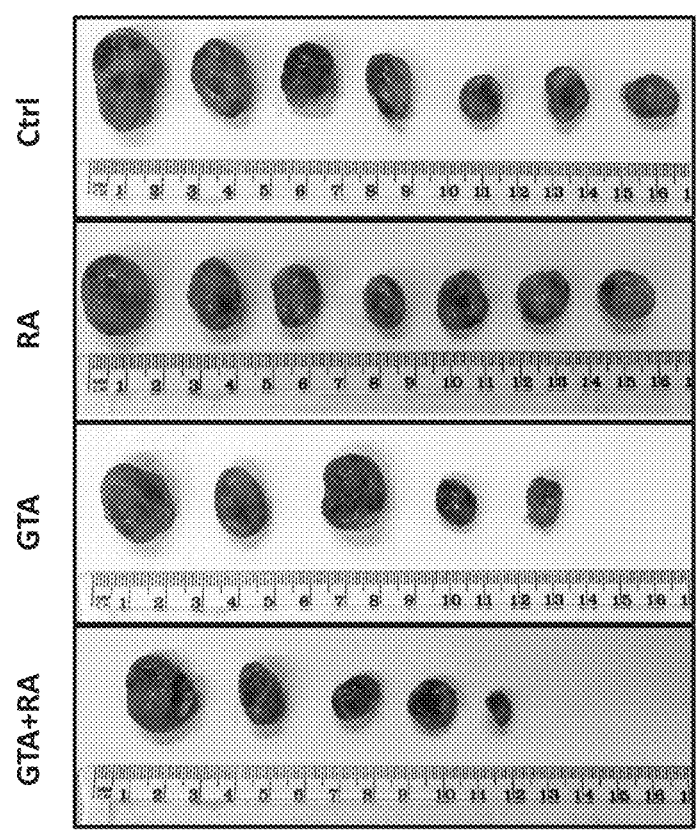
FIG. 13. Tumor image of NSG xenograft mice that received various drug formulations.

In vivo anti-tumor effect of combination of RA and acetate supplementation. Next, we investigated whether acetate supplementation can improve the efficacy of RA in vivo. CHP134 cells were implanted to the flanks of NSG mice and allowed to grow for 3 weeks to reach a volume of ~150 mm³. Then, mice were randomized in four treatment groups: DMSO, RA, GTA or RA+GTA. After 23 days' treatment, RA treatment alone didn't show anti-tumor effect (FIGS. 7A and B, FIG. 13. Combination of GTA and RA resulted in a slight decrease of average tumor weight compared to RA treatment group. However, the p-value did not reach statistical significance (p=0.106), possibly due to the large variation of tumor weight in each group and small sample size (FIG. 7B). The mice body weight in GTA+RA group slightly decreased when comparing to control group (FIG. 7C), and one mouse in GTA+RA group died during the study. These observations suggest that combination of RA and GTA treatment might have a potential toxicity in mice. Pharmacokinetic study showed a relative short half-life of RA. The blood RA concentration reach the peak at 30 min after i.p. injection and maintained a concentration above 10 uM for around 2 h. At 6 h after injection, the blood RA concentration reduced to the basal level (FIG. 7D). LC-MS analysis of the plasma samples from control and GTA treatment group indicated a slight increase of plasma acetate concentration by oral GTA administration, though the p-value did not reach statistical significance (FIG. 7E). One possible explanation is that GTA-derived acetate was primarily trapped by liver due to the high activity of ACSSs.

α-ketoglutarate reduces histone hypermethylation under hypoxia, but cannot restore histone acetylation or differentiation marker expression. A gain-of-function point mutation on cytoplasmic isocitrate dehydrogenase (IDH1) or mitochondrial isocitrate dehydrogenase (IDH2) grants the mutant enzyme the ability to generate D-2-hydroxyglutarate (D2HG). Since D2HG has a similar chemical structure as α-ketoglutarate (αKG), it can inhibit αKG-dependent enzymes, including TET enzymes and Jumonji domain-containing histone demethylases (JMJDs), leading to DNA and histone hypermethylation that block cellular differentiation. Recently, it was reported that tumor cells generated the L-enantiomer of 2-hydroxyglutarate (L2HG) under hypoxic conditions. L2HG also inhibits α-KG dependent enzymes including JMJDs to cause histone hypermethylation, which may lead to gene expression silencing. We wanted to test whether hypoxia also inhibited differentiation through histone methylation. Our results indicated hypoxia increased histone methylation markers in both CHP134 and SMS-KCNR cells (FIG. 8A), which may result from the depletion of αKG and production of 2HG under hypoxia (FIG. 8B). Adding a cell-permeable αKG analog Dimethyl-α-ketoglutarate (DMKG) reduced histone hypermethylation upon hypoxia but did not significantly increase histone acetylation (FIG. 8C). In addition, DMKG supplementation did not restore the expression of NGFR and SNCG under hypoxia (FIG. 8D). These data indicate that inhibition of histone hypermethylation is not sufficient to restore the expression of differentiation markers under hypoxia, histone acetylation might be the limiting factor for RA-induced cell differentiation under hypoxia.

Cell differentiation is the process that a stem/progenitor cell becomes morphologically and functionally specialized. Proper cell differentiation process requires a signaling cascade to activate the transcriptional machinery and the accessibility to chromosome. Together tissue-specific differentiation markers will be expressed, and cells can differentiate. Previous studies have reported that significant metabolic reprogramming occurs during cell differentiation. Generally, undifferentiated cells primarily utilize aerobic glycolysis, but switch to oxidative phosphorylation when they are induced to differentiate. The distinct metabolic phenotype between differentiated cell and undifferentiated cell indicated a critical role of mitochondrial metabolism in differentiation.

It was a century ago when Otto H. Warburg first published his discovery that tumor cells convert large amounts of glucose to lactate through fermentation. The Warburg effect is truly a hallmark that is identified in all kinds of cancer cells. However, the exact role of the Warburg effect in tumorigenesis has remained an enigma. The generation and excretion of lactate would appear be a waste of carbon backbone and energy that is needed for proliferation. The discovery that loss or repression of mitochondrial pyruvate carrier (MPC) in cancer provided an early clue. It has been reported that overexpression of MPC could reduce cancer cells growth and downregulates stemness markers. Oppositely, knocking out MPC or using an MPC inhibitor promotes stem cell function and organoid formation. These data suggest that preventing pyruvate entry into mitochondria is critical for stemness maintenance. However, it's unclear how this event controls cell fate decision, and how other tumor cells without MPC downregulation maintain stemness and dedifferentiation state.

As Warburg and others pointed out, low oxygen is one way of inhibiting respiration and causing the Warburg effect. Hypoxia is a common feature of all solid tumors. It has been well established that hypoxia stabilizes HIF to reprogram cellular metabolism, inhibiting mitochondrial respiration but promoting glycolysis and lactate production. HIF-1-dependent induction of PDKs plays a key role in this metabolic reprogramming and cellular adaptation to hypoxia. While previous studies on PDKs focused on how they regulate entiation markers expression and neuron differentiation morphology when coapplied with RA. Based on these findings, we propose that when combined with differentiation therapy, acetate supplementation turns tumor cells' strength into a weakness, promoting differentiation in tumor cells that display a high demand for exogenous acetate. In addition to neuroblastoma, RA and other retinoids have shown promising anti-cancer effects in cell lines or preclinical models of other types of solid tumors, providing a broad basis for this combination therapeutic strategy.

Materials and Methods

Antibodies and reagents. The antibodies and reagents used in this study are listed in Table 1.

| Antibodies | Source | Identifier |
|---|---|---|
| Anti-Acetyl-Histone H3 antibody | Millipore | Cat# 06-599 RRID: AB_2115283 |
| Anti-Acetyl-Histone H3, (Lys9) antibody | Cell Signaling Technology | Cat# 9649, RRID: AB_823528 |
| Anti-Acetyl-Histone H3 (Lys27) (D5E4) antibody | Cell Signaling Technology | Cat# 8173, RRID: AB_10949503 |
| Anti-Histone H3 antibody | Cell Signaling Technology | Cat# 3638, RRID: AB_1642229 |
| Anti-Tri-Methyl-Histone H3 (Lys9) (D4W1U) antibody | Cell Signaling Technology | Cat# 13969, RRID: AB_2798355 |
| Anti-Histone H3, Trimethyl (Lys27) antibody | Cell Signaling Technology | Cat# 9733, RRID: AB_2616029 |
| Anti-Pyruvate Dehydrogenase E1-alpha subunit (phospho S293) antibody | Abcam | Cat# ab92696, RRID: AB_10711672 |
| Anti-Pyruvate Dehydrogenase (C54G1) antibody | Cell Signaling Technology | Cat# 3205, RRID: AB_2162926 |
| Anti-beta3-Tubulin (D71G9) antibody | Cell Signaling Technology | Cat# 5568, RRID: AB_10694505 |
| Anti-MAP2 antibody | Cell Signaling Technology | Cat# 4542, RRID: AB_10693782 |
| Anti-PDK1 antibody | Enzo Life Sciences | Cat# ADI-KAP-PK112-D, RRID: AB_2039453 |
| Anti-beta-Actin (8H10D10) antibody | Cell Signaling Technology | Cat# 3700, RRID: AB_2242334 |
| Reagents | Source | Catalog |
| 13-cis-Retinoic acid | Sigma-Aldrich | R3255 |
| Sodium acetate | Sigma-Aldrich | S2889 |
| Glyceryl triacetate | Sigma-Aldrich | 90240 |
| Dimethyl 2-oxoglutarate | Sigma-Aldrich | 349631 |
| Sodium dichloroacetate | Sigma-Aldrich | 347795 |
| Sodium acetate-13C2 | Sigma-Aldrich | 282014 |
| pLKO.1-puro Empty Vector | Sigma-Aldrich | SHC001 |
| PDK1 shRNA #1 | Sigma-Aldrich | SHCLNG-NM_002610 TRCN0000006261 |
| PDK1 shRNA #2 | Sigma-Aldrich | SHCLNG-NM_002610 TRCN0000194672 |
| PDK1 shRNA #3 | Sigma-Aldrich | SHCLNG-NM_002610 TRCN0000196635 |
| PDK1 shRNA #1 | Sigma-Aldrich | SHCLNG-NM_005391 TRCN0000000260 |
| PDK3 shRNA #2 | Sigma-Aldrich | SHCLNG-NM_005391 TRCN0000314584 |
| PDK3 shRNA #3 | Sigma-Aldrich | SHCLNG-NM_005391 TRCN0000314596 |
| D-GLUCOSE (U-13C6, 99%) | Cambridge Isotope Laboratories | CLM-1396 |
| Puromycin | ThermoFisher | A1113803 |
| NGFR Taqman probe | ThermoFisher | Hs00609976_m1 |
| SNCG Taqman probe | ThermoFisher | Hs00268306_m1 | mitochondrial activity and cell survival, here we demonstrated that induction of PDKs was also critical in regulating chromatin remodeling and cell differentiation. Treatment with PDKs inhibitor DCA restored histone acetylation under hypoxia, highlighting the potential application of DCA in combination with RA-based differentiation therapy in neuroblastoma treatment.

Many cancer cells overexpress ACSS2 to utilize environmental acetate as a fuel of biosynthesis. Here we demonstrated that acetate or GTA supplementation not only restored histone acetylation but also restored neuron differ- Cell culture and RNAi. CHP134 and SMS-KCNR cells were obtained from Dr. John M. *Maris*' laboratory (Children's Hospital of Philadelphia) and Dr. C. Patrick Reynolds' laboratory (Texas Tech University Health Sciences Center), respectively. Certificate of analysis is available from each group. Both cell lines were cultured in DMEM/F12 supplemented with penicillin, streptomycin, 10% FBS. Stable CHP134 cells expressing PDK1 or PDK3 shRNA were generated through infection with lentivirus and puromycin selection. To obtain the shRNA-expressing virus, pLKO-shRNA vectors (Sigma-Aldrich) were cotransfected with the third-generation lentivirus packaging plasmids (pMDLg, pCMV-VSV-G and pRsv-Rev) into HEK293T cells using FuGENE 6 Transfection Reagent (Promega). Media was changed after 24 h and viral supernatant was collected at 48 h. Target cells were infected by viral supernatant (diluted 1:1 with DMEM/F12; 6 µg/ml polybrene). Fresh media was added after 24 h and cells was selected with 2 µg/ml puromycin for 48 h. Thereafter, cells were maintained in DMEM/F12 with 1 µg/ml puromycin.

Protein isolation and western blot. Cells were washed with PBS buffer and lysed with Harvest lysis buffer supplemented with Halt inhibitors for 5-10 min. Cell lysate was centrifuged at 5000 rpm for 5 min at 4° C. The supernatant containing cytosolic proteins was transferred to a new EP tube. The insoluble part contains nuclear proteins and was further lysed with nuclear lysis buffer for 5 min at 4° C. Then the lysate was sonicated in water-bath at 4° C. for 6 cycles (1 cycle=30 s sonication and 30 s cooldown). After sonication, the cell lysate was centrifuged at 15000 rpm for 10 min. Protein concentration was determined by BOA assay. 1 µg nuclear proteins or 1 µg cytosolic proteins were boiled in loading buffer with reducing reagents, then separated with SDS-PAGE. Protein were transferred onto a nitrocellulose membrane. After blocking in 5% non-fat milk for 1 hour, the first antibody was applied. After 3×TBST washes, HRP-conjugated secondary antibodies were applied. Signals were detected with an ECL kit. The complete antibody list is in table 1.

RNA Isolation, Reverse Transcription, and Real-Time PCR. Total RNA was isolated from tissue culture plates according to the TRIzol Reagent (Invitrogen) protocol. 3 µg of total RNA was used in the reverse transcription reaction using the iScript cDNA synthesis kit (Bio-Rad). Quantitative PCR amplification was performed on the Prism 7900 Sequence Detection System (Applied Biosystems) using Taqman Gene Expression Assays (Applied Biosystems). Gene expression data were normalized to 18S rRNA.

Neurite outgrowth assay. For the differentiation of neuroblastoma cells, $1\times10^5$ CHP134 or SMS-KNCR cells were plated in 6 well-plate. After overnight incubation, cells in hypoxia treatment group were pre-incubated in 0.5% O2 hypoxia chamber for 6 h. Then RA was added to reach a final concentration of 10 µM. After 48 h treatment, images were taken through an Olympus phase contrast microscope (×20 magnification). The lengths of the neurites were traced and quantified using the ImageJ plugin NeuronJ. Within each sample, total neurite length was measured and normalized by the number of cell bodies, mean value from biological triplicates was reported.

Immunofluorescence staining. CHP184 cells were seeded into 8-champer slides with a density of 6000 cells/well and incubated with indicated treatment for 3 days. Cells were fixed with 4% PFA in 0.1% PBS-tween at room temperature for 30 min followed by permeabilization with 0.1% Triton X-100 in PBS at room temperature for 10 min. The cells were washed with PBS twice and blocked with 2.5% horse serum at room temperature for 1 hour. Then, cells were subjected to immunofluorescence staining with primary antibody overnight at 4° C. After twice washes with PBS, cells were incubated with Alexa Fluor 594-labeled anti-rabbit secondary antibody (Life Technologies) at room temperature for 1 hour followed by staining with DAP for 20 min. Images were acquired with Leica DMi8 microscope.

RNA Sequencing. The total RNA from four treatment groups (Nor_Ctrl, Nor_RA, Hyp_Ctrl and Hyp_RA, 3 replicates) was extracted using Trizol reagent according to the manufacturer's instructions (n=3). The RNA-seq library was constructed and subjected to 150 bp paired-end sequencing on an Illumina sequencing platform (Novogene). RNA-seq analysis was performed using the kallisto and sleuth analytical pipeline. In brief, a transcript index was generated with reference to Ensembl version 57 for hg19. Paired-end mRNA-seq reads were pseudo-aligned using kallisto (v0.42.4) with respect to this transcript index using 100 bootstraps (-b 100) to estimate the variance of estimated transcript abundances. Transcript-level estimates were aggregated to transcripts per million (TPM) estimates for each gene, with gene names assigned from Ensembl using biomaRt. Differential gene expression analysis was performed using the sleuth R package across pairwise groups (normoxia DMSO vs. normoxia RA, normoxia DMSO vs. hypoxia DMSO, normoxia RA vs. hypoxia RA) using Wald tests, with significant hits called with a sleuth q-vaulue<0.05 and fold change estimate b>abS(In(2)).

ATAC-seq. ATAC-seq was performed and analyzed as previously described (n=2). Reads were trimmed with cut-adapt version 1.8.1 with flags -u -50 -U -50 -a CTGTCTCT-TATACACATCTCCGAGCCCACGAGAC -A CTGTCTCTTATACACATCTG ACGCTGCCGACGA -O 5 -m 30 -q 15. Bowtie 2 version 2.3.1 was used to align trimmed reads to hg19 with flags -q -phred33-X 2000 -fr -p 8 -x hg19, followed by samtools sort command. Duplicates were marked with Picard-tools version 1.83, then samtools view with flags -b -f 1 -F12 -L were used to filter mitochondria mapping reads with a bed file containing all chromosomes except chrM. Filtered mapping files are transferred into coverage bigwig file using deeptools with default bin size (10 bps). SPP/phantom was run to obtain the fragment length with maximum Strand cross-correlation. MACS2 callpeak function was then performed with flags -q 0.05 -nomodel-extsize=½ fragment length obtained from SPP. Associate p-values for each peak is generated and extracted from MACS2 output. Ranked gene lists were created from the RNA-Seq and ATAC-Seq datasets following differential testing. Gene set enrichment analysis were performed using the GSEA with the C2 (CP:REACTOME) MSigDB v6.2.

Cell proliferation assay. Cell proliferation was assessed using cell counting (Beckman). Briefly, $2\times10^4$ cells were plated in 24 well-plate and attached overnight ($4\times10^4$ cells per well if 12 well-plate was used). Then cells were treated with various conditions as indicated for 48 h (n=3). Before cell counting, the medium was removed and 100 ul 0.25% trypsin was added to each well for 3 min. 900 µl medium was added to stop digestion, and 100 ul cell suspension was transferred to cell counting vial.

Metabolic tracing study. For glucose isotope tracing, CHP134 cells were pretreated under normoxia or hypoxia for 16 h (n=3). Then the medium was changed to DMEM:F12 with 3.15 g/L $^{13}C_6$-glucose with 10% dialyzed FBS for 3 h. For acetate isotope tracing, the procedure was same as glucose tracing except that the complete DMEM:F12 medium was supplemented with 2 mM $^{13}C_2$-acetate.

Liquid chromatography-mass spectrometry analysis. For the metabolic tracing study, cells were washed with cold PBS, lysed in 80% Ultra LC-MS acetonitrile on ice for 15 min, centrifuged for 10 min at 20,000×g, and supernatant was subjected to mass spectrometry analysis. Liquid chromatography was performed using an Agilent 1290 Infinity LC system (Agilent, Santa Clara, US) coupled to a Q-TOF 6545 mass spectrometer (Agilent, Santa Clara, US). A hydrophilic interaction chromatography method (HILIC) with a BEH amide column (100 ×2.1 mm i.d., 1.7 µm; Waters) was used for compound separation at 35° C. with a flow rate of 0.3 ml/min. The mobile phase A consisted of 25 mM ammonium acetate and 25 mM ammonium hydroxide in water and mobile phase B was acetonitrile. The gradient elution was 0-1 min, 85 % B; 1-12 min, 85% B→65% B; 12-12.2 min, 65% B→40% B; 12.2-15 min, 40% B. After the gradient, the column was re-equilibrated at 85% B for 5 min. The overall runtime was 20 min, and the injection volume was 5 µL. Agilent Q-TOF was operated in negative mode and the relevant parameters were as listed: ion spray voltage, 3500 V; nozzle voltage, 1000 V; fragmentor voltage, 125 V; drying gas flow, 11 L/rain; capillary temperature, 325° C., drying gas temperature, 350° C.; and nebulizer pressure, 40 psi. A full scan range was set at 50 to 1600 (m/z). The reference mass were 119.0363 and 980.0164. The acquisition rate was 2 spectra/s. Targeted analysis, isotopologues extraction and natural isotope abundance correction were performed by Agilent Profinder B.08.00 (Agilent Technologies).

For acetate measurement, 10 ul of serum was mixed with 10 ul of 50 uM $^{13}C_2$-acetate. Then, the mixture was precipitated by the addition of 80 ul acetonitrile and centrifuged for 10 min at 20,000×g. 80 ul supernatant was transferred to a new tube and derivertized according to the published protocol. 2 ul sample was subjected to mass spectrometry analysis using Agilent 1290 coupled to Q-TOF 6545. ZORBAX Eclipse Plus 018 columns (50×2.1 mm, 1.8 µm, Agilent) was used for compound separation at 35° C. with a flow rate of 0.3 ml/min. The mobile phase were 5 mM ammonium formate and 0.1% formic acid in water (A) and 90% acetonitrile (B). The gradient elution was 0-0.5 min, 10% B; 0.5-4 min, 10% B→90% B; 4-7.5 min, 90% B. After the gradient, the column was re-equilibrated at 10% B for 2.5 min. Agilent Q-TOF was operated in positive mode with ion spray voltage at 3500 V. The ratio of acetate to $^{13}C_2$-acetate was calculated using Agilent Profinder software B.08.00.

For 13-cis-retinoic acid measurement, serum samples were collected at 0.5 h, 1 h, 2 h and 6 h after RA injection (10 mg/kg, i.p.). 10 ul serum was mixed with 90 ul extraction buffer (ethyl acetate:n-hexane:IPA, 30:60:10). After 20 min on a shaker at 120 rpm, the mixture was centrifuged at 5000 g for 5 min. The organic layer was collected into a new tube and dried using speed vacuum. The residue was reconstituted with 100 ul of 5 mM ammonium formate in water/acetonitrile (1:1). 5 ul sample was subjected to mass spectrometry analysis using Agilent 1290 coupled to QQQ 6470. ZORBAX Eclipse Plus 018 columns (50×2.1 mm, 1.8 µm, Agilent) was used for compound separation at 35° C. with a flow rate of 0.3 ml/min. The mobile phase was 5 mM ammonium formate and 0.1% formic acid in water (A) and 90% acetonitrile (B). The gradient elution was 0-0.5 min, 50% B; 0.5-2 min, 50% B→90% B; 2-4.8 min, 90% B. After the gradient, the column was re-equilibrated at 50% B for 2.2 min. Agilent QQQ 6470 was operated in positive mode with ion spray voltage at 3000 V. The MRM transitions were 301.2→159.1/205.1. Data was processed by Agilent MassHunter Quantitative Analysis for QQQ B.07.01. (Agilent Technologies)

Mouse xenograft model. In viva studies were performed in accordance with protocols approved by the Institutional Animal Care and Use Committee at Stanford University and in compliance with all regulatory standards, 6 to 8-week-old male NSG mice were provided by Dr. Erinn Rankin. $2 \times 10^6$ CHP134 cells suspended in 1004 of RPMI-1640 with 50% Matrigel (BD Biosciences) were implanted subcutaneously into the dorsal flank of the mice. Tumor growth was recorded using digital caliper every other day, and tumor volumes were estimated using the formula: $(L \times W^2)/2$, where L=length and W=width of tumor. The animals were randomized into 4 groups (Control, RA, GTA and GTA+RA) when the tumor volumes reached approximately 150 mm³. 10 mg/kg RA or DMSO vehicle was injected intraperitoneally daily for 3 weeks. Mice received GTA in the drinking water (5% by weight).

Statistics. For cell proliferation and MS experiments, three biological repeats were used for data analysis. Results were represented as mean±SD of three biological repeats. The Student's t-test will be performed to determine the significance between groups (two tailed, unequal variance).

Data availability. RNA-Seq data are available on NCBI Sequence Read Archive. (BioProject Accession No.: PRJNA596588). ATAC-Seq data are available on NCBI Sequence Read Archive. (BioProject Accession No.: PRJNA596881)

Example 2

Hypoxic Cancer Cells are Sensitized to Retinoid Therapy by Metabolic Interventions This research identifies therapeutic strategies for the treatment of neuroblastoma. Cell differentiation is the process that a stem cell becomes specialized cells. This process is dysregulated in cancer cells. A proper differentiation requires a signaling cascade to activate the transcriptional machinery, and the accessibility to chromosome. Together tissue-specific differentiation marker will be expressed, and cells can differentiate. Retinoids are chemicals that are related to vitamin A, which has been has been utilized to induce differentiation of neuroblastoma cells for over 15 years. However, not all the neuroblastoma patients benefits from retinoid therapy. Tumor hypoxia is a negative prognostic and predictive factor and is associated with a more aggressive phenotype in various tumor entities including neuroblastoma, which is a leading cause for the resistance to therapy. Tumor microenvironment factors, especially tumor hypoxia, may be the leading cause for the resistance to retinoid therapy. The data in Example 1 demonstrated that hypoxia blocks retinoic acid (RA) induce neuroblastoma cell differentiation. Under hypoxia, cancer cells will reprogram cellular metabolism to adapt the stress condition. We have proved hypoxia altered histone modification and this alterations can be rescued by metabolic interventions. The effect of multiple nutrients supplementation alone or combined with retinoid on tumor progression is evaluated. The compound or nutrients used in this study includes 13-cis-retinoic acid, glyceryl triacetate, and nicotinamide riboside.

80 athymic nu/nu female mice (8-12 weeks) are used for the in vivo tumor microenvironment experiments. 2 million of CHP-134 cells are injected subcutaneously into the right flanks of nude mice.

After injection, tumor size is measured every two days. The tumor volume is calculated by the following formula: Volume (mm³)=4/3 #r3, r=diameter/2. When the mean tumor volume reaches approximately 300 mm³ (diameter=8.3 mm) the mice are randomly assigned by the random number table method into eight groups with approximately equivalent ranges of tumor volume between groups. There are 8 groups including control, NAD+ precursor nicotinamide riboside (NR), acetylating reagent glyceryl triacetate (GTA), NR+GTA, 13-cis-RA, 13-cis-RA with NR, 13-cis-RA with GTA, and 13-cis-RA.

Each publication cited in this specification is hereby incorporated by reference in its entirety for all purposes.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention, which will be limited only by the appended claims As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

What is claimed is:

1. A method for the treatment of neuroblastoma in an individual, the method comprising:
   contacting a population of cancer cells with a synergistically effective amount of (i) isotretinoin; and (ii) glyceryltriacetate (GTA), effective to increase differentiation of the cancer cells, wherein the treatment is synergistic relative to the level of differentiation with retinoic acid administered in the absence of GTA.

2. The method of claim 1, wherein the isotretinoin is orally administered.

3. The method of claim 1, wherein the dose of isotretinoin is from 10 to 500 mg/m$^2$/day.

4. The method of claim 3, wherein the dose of isotretinoin is decreased relative to the effective dose in the absence of GTA.

5. The method of claim 1, wherein the GTA is orally administered.

6. The method of claim 5, wherein the dose of GTA is from 25 to 1000 mg/kg/daily.

7. The method of claim 1, wherein the isotretinoin and GTA are concomitantly administered.

8. The method of claim 7, wherein the isotretinoin and GTA are co-formulated.

9. The method of claim 7, wherein the isotretinoin and GTA are separately formulated.

10. The method of claim 1, wherein the neuroblastoma is high risk neuroblastoma.

11. The method of claim 1, wherein the treatment provides for increased overall survival of the individual.

12. The method according to claim 1, wherein the individual is a human.

* * * * *